United States Patent
Califano et al.

(10) Patent No.: US 7,801,747 B2
(45) Date of Patent: Sep. 21, 2010

(54) METHODS AND SYSTEMS FOR MANAGING INFORMED CONSENT PROCESSES

(75) Inventors: Andrea Califano, New York, NY (US); Aristidis Floratos, Astoria, NY (US); David Wang, Killdeere, IL (US); Peter Young, New York, NY (US); Arthur Holden, Winnetka, IL (US)

(73) Assignee: Cerner Innovation, Inc., Overland Park, KS (US)

( * ) Notice: Subject to any disclaimer, the term of this patent is extended or adjusted under 35 U.S.C. 154(b) by 357 days.

(21) Appl. No.: 11/438,677

(22) Filed: May 22, 2006

(65) Prior Publication Data

US 2006/0271406 A1   Nov. 30, 2006

Related U.S. Application Data

(63) Continuation of application No. 10/122,711, filed on Apr. 15, 2002, now abandoned.

(60) Provisional application No. 60/283,809, filed on Apr. 13, 2001.

(51) Int. Cl.
    *G06F 19/00* (2006.01)
(52) U.S. Cl. .............................. 705/3; 705/2; 600/300; 434/350; 713/165
(58) Field of Classification Search .................. 705/3, 705/2; 434/350; 713/165
    See application file for complete search history.

(56) References Cited

U.S. PATENT DOCUMENTS

| | | | |
|---|---|---|---|
| 5,999,909 A * | 12/1999 | Rakshit et al. | 705/2 |
| 6,472,421 B1 * | 10/2002 | Wolozin | 514/451 |
| 6,820,235 B1 * | 11/2004 | Bleicher et al. | 715/236 |
| 6,874,085 B1 * | 3/2005 | Koo et al. | 713/165 |
| 2002/0046054 A1 * | 4/2002 | Morand et al. | 705/1 |

\* cited by examiner

*Primary Examiner*—Vanel Frenel
(74) *Attorney, Agent, or Firm*—Shook, Hardy & Bacon L.L.P.

(57) ABSTRACT

The systems and methods provide a dynamic process for obtaining and managing informed consent documentation. In general, the dynamic informed consent process (DICP) makes use of an intermediary organization, e.g., a trusted intermediary, which: (a) provides ICFs which have been dynamically generated for a specified trial or medical procedure and based on particular state or federal requirements, if any; and (b) archives copies of signed ICFs. In certain preferred embodiments, there may also be a procedure to provide training materials, such as audio or video presentations, to be viewed by prospective participants. In certain preferred embodiments, the process also includes contacting subjects who have signed ICFs in the event that there is a change of circumstance which the subject may deem material to whether s/he would continue to consent, or whether the participant needs to provide a different type of consent to participate in particular event or trial.

23 Claims, 17 Drawing Sheets

METHODS AND SYSTEMS FOR MANAGING INFORMED CONSENT PROCESSES

CROSS-REFERENCE TO RELATED APPLICATIONS

This application is a continuation of U.S. application Ser. No. 10/122,711, filed Apr. 15, 2002, now abandoned which claims the benefit of U.S. Provisional Application No. 60/283,809, filed Apr. 13, 2001 and relates to U.S. application Ser. No. 09/939,200 filed: Aug. 24, 2001, the entire contents of both applications being herein incorporated by reference.

BACKGROUND OF THE INVENTION

Sequencing of the human genome will generate an avalanche of genetic information to be linked with information about microbial, chemical, and physical exposures; nutrition, metabolism, lifestyle behaviors, and medications. Advances in DNA sequencing technology and in the understanding of the human genome are ushering in a new era of genomic medicine, one with dramatic potential to not only benefit society through research involving human subjects, but also to cause economic or psychosocial harms to clinical subjects and their families. While in some cases such information may be beneficial to research subjects and their families, there is also potential for misinterpretation or misuse.

In today's medical environment, a health practitioner or clinical trial sponsor would (or at least should) never consider performing a medical procedure, such as a surgical or diagnostic procedure, on a patient, or putting that individual in a clinical trial, without first obtaining informed consent. This is not only important from a risk management perspective, but is basic to the proper practice of medicine.

Special concerns have arisen about the process of informed consent, particularly when the risks and benefits of research participation may not be fully known. Concerns have also arisen about how best to prevent the preliminary or premature release of research results and to protect the privacy of individuals who choose to participate in genetics research. Current guidance and protections need to be enhanced to deal with the special considerations related to genetics research.

The information most often provided in obtaining consent to participate in clinical trial includes the research procedure; the purposes, risks, and anticipated benefits; alternative procedures (where therapy is involved); and a statement offering the opportunity to ask questions and to withdraw from the research at any time. Federal regulations (45CFR46 and 10CFR745) require the disclosure of a number of issues in any informed consent document. They include such issues as potential benefits of the research, potential risks to the donor, control and ownership of donated material, long-term retention of donated material for future use, and the procedures that will be followed. In addition, there are several other disclosures that are of special importance for donors of DNA for large-scale sequencing. These include:

The meaning of privacy and confidentiality of information in the context of large-scale DNA sequencing, and how these issues will be addressed;

The lack of opportunity for the donor to later withdraw the libraries made from his/her DNA or his/her DNA sequence information from public use;

The absence of opportunity for information of clinical relevance, e.g., information regarding susceptibility to disease, etc., to be provided to the donor or her/his family;

The possibility of unforeseen risks; and

The possible extension of risk to family members of the donor or to any group or community of interest (e.g., gender, race, ethnicity) to which a donor might belong.

Comprehension, the manner and context in which information is received, is also another important issue in dealing with informed consent. Many of the standard informed consent forms currently used have often fatal practical limitations and they may be inconsistently applied. Typically the forms are modified for each specific medical, dental or psychiatric procedure. While this is efficient, it rarely takes into account the impacts of the differing information to be conveyed, the differing manners in which it must be delivered (if read), and the differing attitudes of the patient. Each of these naturally affect the dependability of the form. In addition, as each doctor tries to alter a general form for a specific procedure, personal biases can detract from the real goal of the process. Even if each of these limitations were recognized, until the present invention, it simply would not have been practical to tailor a document not only doctor to doctor, but also from day to day, and from patient mood to patient mood. This latter aspect—that a given patient might have different needs from day to day or hour to hour—has been an aspect that, until the present invention, those skilled in the art could not readily address. Those skilled in the art, the doctors and lawyers, simply believed it was not possible to accommodate the needs of the patient to this degree. While the need for controlled consistency in this area has been openly sought by consumer protection groups, medical groups, and malpractice insurance carriers, until the present invention it was not deemed practical to attempt to utilize a technique which could be varied to suit each specific occasion.

Systems and methods that address these issues and develop guidelines and frameworks for ensuring the safe and appropriate use of genetic information are crucial to the success of large use of genetic information are described below.

SUMMARY OF THE INVENTION

The systems and methods described herein include, inter alai, systems that allow a person to control the use of their medical and biological data on a continuous, selective and dynamic manner. Specifically, the systems described herein include systems that allow a person to store or have stored into a database their medical and biological data. Along with the medical and biological data, the person stores a grant of consent that indicates the types of activities and uses to which the person agrees or consents. The database links the stored data with the granted consent. As it can be difficult for a person to understand what kind of consent should be granted, in one embodiment, the system helps the person determine what grant of consent to provide. To this end, the system can guide the person through a process that helps the person complete a consent form that indicates the different allowed uses for the data. In a preferred embodiment, each grant of consent includes an indication as to whether the person is willing to be recontacted at a later to date, wherein the re-contact is typically for the purpose of requesting the person to consent to a new treatment or use of their medical, genetic, demographic or biological data. The grant of consent may be stored in a database along with and in association with the medical, genetic, and/or biological data.

The systems further include a query mechanism that an interested party, such as a researcher, medical professional or some other person may use to query the stored data to identify individuals of interest. In one example, a researcher conducting a study to determine the efficacy of a particular treatment or regime, searches through the data to identify individuals that may have a medical condition, a medical history, a genetic marker or some other condition or conditions of interest to the researcher. The query, when completed, provides a list of human subjects that meet the criteria. To protect privacy, the actual identities of the human subjects may be kept secret. In one practice, each person that has provided data receives a client code that may be employed to distinguish that person from the others that have stored data in the system. Optionally, the code may also be employed to re-contact the person. However, the code by itself lacks information that may be employed to identify the person.

As can be seen from the above, the systems and methods described herein allow, among other things, a medical professional to identify persons that may benefit from taking part in a research study and to anonymously re-contact the identified persons with a request that they consent to the required use of their medical and biological data.

In particular, in one aspect the invention provides processes for obtaining informed consent from a human subject for an action or a procedure. The human subject may be any person that can give consent for an action or procedure. Thus it can be the participant themselves, as well as a guardian, parent, or court appointed agency. The action that may be consented to can be any action or procedure, such as for example a surgical procedure or a research study. Further, consent may be provided to allow the system of individuals The process for obtaining the informed consent may include having the human subject stored data that is representative of medical and genetic information into a data memory and having the human subject indicate a grant of informed consent to be associated with the stored data. The process may then allow the querying of the stored data to determine the grant of informed consent associated with that stored data, and the allow the determination of whether the provided grant of consent is sufficient for the action and includes a grant of consent to recontact the human subject. The process may then allow, in response to the determined grant of consent, the re-contacting of the human subject to request the human subject to change the associated grant of informed consent. Typically the request is that the human subject change the associated grant of informed consent to a grant of consent that is appropriate, or required, for an action or procedure that is being proposed by the interested party.

In further embodiments, the process may include having a trusted third party control access to the stored medical and genetic data. The trusted third party may also broker correspondence between the interested parties and the human subject, thus providing greater security that interested parties will not determine the identity of the human subjects that have provided data. Thus in certain practices, the processes allow for contacting the human subjects by having a trusted third party contact the human subjects.

To further provide for privacy and anonymity, the processes may allow for encrypting the data, or portions of the data, that is stored in the data memory. In this process, the human subject may be allowed to store portions of the medical and genetic data as clear text and other portions in an encrypted format. Optionally, the human subjects may further be able to control which portions of the stored data may be searched by an interested party and which portions of the stored data are to remain private. In further practices, the human subject may further designate controls over what types of interested parties may look at certain portions of the stored data. Thus, the human subject may allow certain types of interested parties, such as academic researchers, to view all the stored data while other types of interested parties, such as pharmaceutical companies, may be provided more limited access to the stored data. In either case however, data that is encrypted for storage, in some embodiments, may be made available in clear text format to the query mechanism to allow for searching on encrypted data. Thus, in certain embodiments, the human subject encrypts data stored within the data memory for the purpose of protecting that data while it is stored. However, during queries run by interested parties, the processes may allow the interested parties to search on encrypted data, typically by decrypting the data during the data query process, so that this data may be viewed by the interested parties that the human subject has authorized to view that data.

In a further practice, the process will allow storing medical and biological data as well as contact data that may be employed for recontacting the human subject. The contact data may be an address, such as an email address, a post address, a patient code assigned to the human subject, an address for the human subject's physician and/or any type of identity information that may be employed for identifying the human subject. The method for contacting the human subject may vary according to the application and may include, email, telephone, post mail, and, in a preferred embodiment, by posting messages on a portal, typically a web-based network portal, that the human subject is authorized to access.

In a typical practice, the processes described herein are capable of handling data for a plurality of human subjects. Thus a plurality of human subjects may store data within the data memory. The data in the data memory may be made available to authorized interested parties for the purposes of identifying human subjects that may benefit from an action or procedure being carried out by the interested party. Thus, interested parties may employ the processes described herein for determining which of the human subjects that have stored data within a data memory have data that meets certain criteria set out in the query. The processes may return the grant of consent that had been earlier provided by the human subjects. The process allows for contacting the identified human subjects with a request to change the granted level of consent.

Optionally, the process may contact the identified human subjects, thus providing the interested party with a platform for identifying and contacting human subjects that may benefit from participating in an action, procedure or study. When contacting the human subjects that process may provide to the human subjects information that is representative of the required grant of consent that that human subjects will need to agree to in order to participate in the action or procedure. The processes therefore will allow the human subject to change consent stored in the data memory. In the processes described herein the human subject may change the consent stored in the data memory in response to a request to change the consent, or, optionally, at their own volition and unprompted. The human subject can change the consent data in any manner that they choose, including expanding the granted level of access and rights to the stored data, reducing the granted level of access and rights, and eliminating altogether the ability to access or use the data. Additionally, the user can expand, restrict, or eliminate the types of parties that are authorized to query the data that they have stored, or to recontact them. For example, the human subject may restrict access to data to only trusted intermediaries. Thus it will be understood to those of ordinary skill in the art that the systems and methods described herein provide a platform that offers the human subject a substantial amount of flexibility in controlling how their data is used and who can use it.

In a further aspect, the invention will be understood to provide systems for managing access to medical record and genetic information of an individual and to allow a researcher or clinician or other biomedical professional to find participants for a study. The systems may comprise a database that has storage for medical record an biological data of an individual and that has storage for consent data that is representative of a limited grant of informed consent provided by the individual for the data. The database can link the consent data with the stored medical record and biological data. The systems further comprise a query tool that allows a researcher to query the medical record data to identify an individual of interest to the study and that returns to the researcher the consent data that is associated with medical record data that matches the query. The system further includes a contact mechanism that can be a computer process, and that allows the biomedical professional to indicate a required grant of consent for the study and to contact the individual and request the individual to grant the necessary informed consent. The system further includes a response process that allows the individual to participant in the study by granting the new consent and associating the new consent with the data provided by the individual.

Optionally, the systems may include data storage for biological sample data, medical data and genetic data. Storage systems for physical storage devices may be incorporated into the systems as well. Thus, in some embodiments refrigeration storage systems for storing samples, such as tissue samples, may be integrated into the systems described herein. In one embodiment, access to the sample storage systems may be controlled as well as monitored by the systems described herein. To this end, these systems may include access control devices that verify access requests against a stored level of informed consent provided by the human subject. The systems may further include a network web server for providing access over a data network. In these embodiments, a web server may be included to provide a portal that gives network access to both researchers and individuals. The portal may a secure website that requires a password and user name to log on to and access. Thus the portal may provide a secure mechanism for allowing authorized individuals to have easy access to the system for the purpose of managing how their data is to be used. At the same time, the web server may be employed as a portal to present information to authorized user. Thus a biomedical professional may be interested in conducting a study and, through querying the stored data, may have identified a group of individuals that may benefit from the study. The biomedical professionals may generate a description of the study and the benefits that it may hold. At the same time the biomedical professionals may create an appropriate informed consent form. The biomedical professionals may deliver to the system the description of the study and the required informed consent form and the system may post the description and informed consent form to each of the individuals identified by the biomedical researcher. Thus in one embodiment, when an authorized user logs on to the portal, they will be presented with a web page that describes a study from which the database query indicates that they may benefit. The web page may further include a link to the required informed consent. At the discretion of the individual, the individual may agree to join the study by granting the required level of consent and having the required level of consent be associated with their stored data. Optionally, the portal may identify the targeted individuals that have granted the required level of request and provide this information to the researcher. In this way, the systems and methods described herein provide a facile system for allowing a biomedical professional to enroll participants into a study or procedure that they are conducting.

DESCRIPTION OF THE FIGURES

The foregoing and other objects and advantages of the invention will be appreciated more fully from the following further description thereof, with reference to the accompanying drawings wherein.

DESCRIPTION OF CERTAIN ILLUSTRATED EMBODIMENTS

Figure 1:
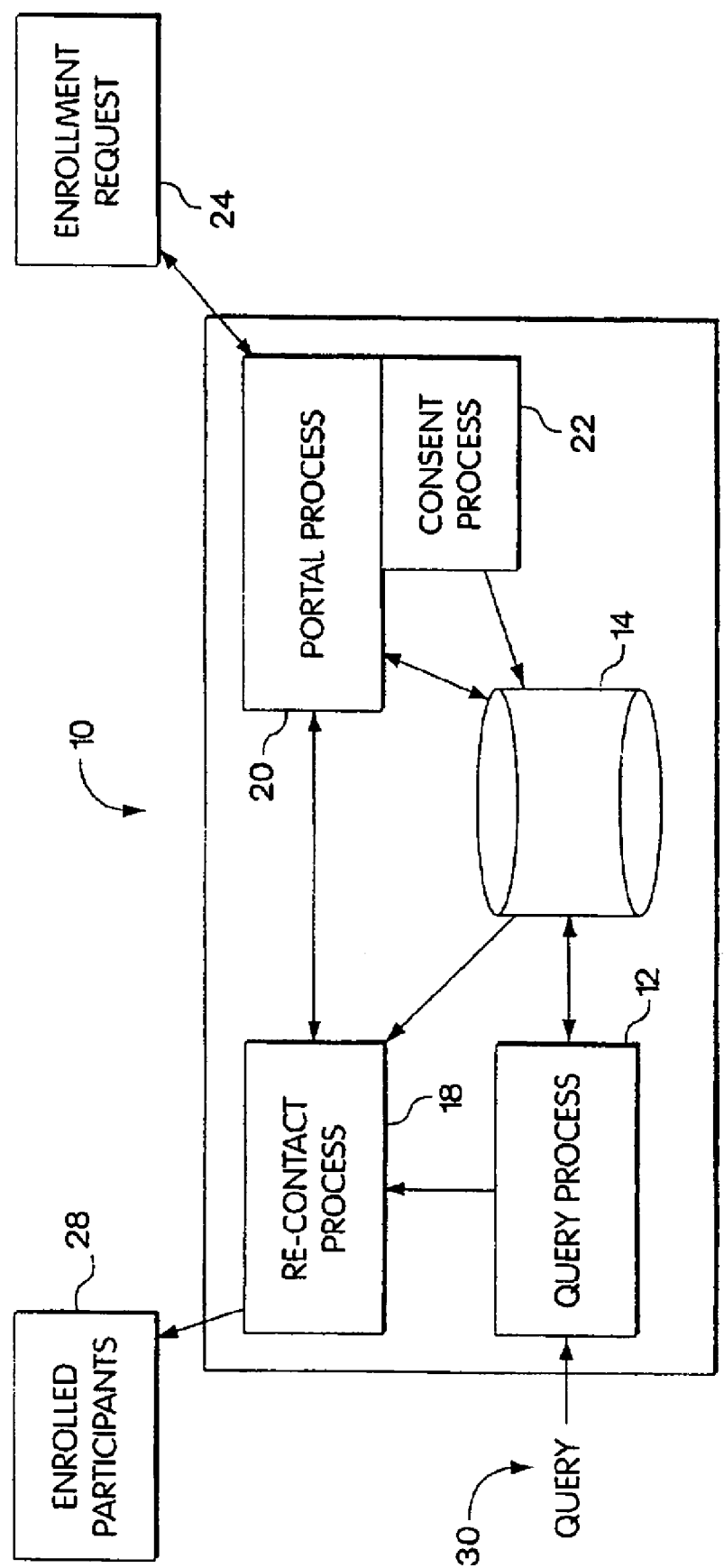
FIG. 1 depicts a first embodiment of a system according to the invention.

Federal and international regulations demand that all individuals participating in clinical procedures, clinical trials or other medical studies sign a formal document, known as the "Informed Consent Form" (ICF). These documents must be signed after the individuals have received (by their physicians as well as by other study-related education specialists) sufficient information to have a reasonable understanding of the non-technical study aspects (e.g., scope, risks, future use of results, future use of the personal and medical information provided by the study participant, etc.). The ICF is to provide a succinct description of these aspects. After signed by an individual, an ICF constitutes formal evidence of the willful and informed decision of the individual to be part of the study. Typically, although option-ally before a study participant at a given site can sign an ICF, an Institutional Review Board (IRB) or Ethics Review Board (ERB) at that site is to approve the study protocol and the ICF.

Obtaining informed consent specifically for the purpose of donating DNA for large-scale sequencing may raise some unique concerns. Because anonymity typically cannot be guaranteed and confidentiality protections are not absolute, the disclosure process to potential donors should clearly specify what the process of DNA donation involves, what may make it different from other types of research, and what the implications are of one's DNA sequence information being a public scientific resource.

The systems and methods described herein provide a dynamic process for obtaining and managing informed consent documentation. In general, although not in all embodiments and practices, the dynamic informed consent process (DICP) makes use of an intermediary organization, e.g., a trusted intermediary, which: (a) provides ICFs which may have been dynamically generated for a specified trial or medical procedure and based on relevant study, state and federal requirements, if any; and (b) archives copies of signed ICFs. In certain embodiments, the processes provide training materials, such as written, audio or video presentations, to be reviewed by prospective participants. In certain embodiments, the process also includes contacting subjects who have signed ICFs in the event that there is a change of circumstance which the subject may deem material to whether s/he would continue to consent, or to recontact participants with a proposal to join another study or to continue with a study as it progresses to a later stage.

An often common complication to any of the above examples of instances which are suitable for use of the subject process is that, because of local regulatory differences among geographic locales, ICFs are to be tailored to the study participant's location (state, country) as well as potentially having to be translated in the participant's native language. To this end, and as described later, the subject systems and processes may be used to generate ICFs which account for such local variations in requirement.

Once created, the subject informed consent process may also be used to manage ICFs for clinical trials. For instance, the systems and processes may be used to deliver information and obtain verification from a prospective participant that s/he understands that the trial is a scientific experiment and there may be risks and dangers to their health and privacy that s/he has been told about the reasons for doing the trial, the identity of the drugs which may be given, the number of visits and the kinds of lab tests required. Additionally and optionally, as different and various types of data may be stored, generated or employed as part of the clinical trial or procedure, including the genotypic data, demographic data, identity data, medical history data and other types of biological data, the ICF is likely to speak to the entities and purposes that are allowed to employ this data. Thus, in certain embodiments, the systems and methods described herein may be used to manage the ICFs for human subjects providing access to genotypic or other individually identifiable phenotypic information, which may be an outcome of, for example, a clinical trial, a diagnostic test, or a healthcare database Likewise, the subject method can be used to manage the ICFs for subjects providing tissue or cells samples for research or diagnostic purposes or for use in a cellular product.

In many instances of clinical trials or genetic testing, ICFs are study-specific and cannot be modified. In these cases, if a new study, Study B, has to be designed to expand on a previous genetic study, Study A (e.g., because new findings indicate that it makes sense to pursue a different avenue), then a new protocol must be generated and approved and a new ICF must be generated and signed by all the study participants. Thus, Study A participants are to be re-contacted to ask their permission to use the material collected during Study A for the new Study B. In the case of the subject invention re-contacting is possible, either directly or, in some embodiments, through a trusted intermediary, as the systems and methods described herein have a link between study participants, their data and, in some cases, their identity. Thus, re-contacting is possible using the systems and methods of the invention.

In still other embodiments, the systems and methods described herein make it possible to dynamically generate ICFs. Thus, the subject systems and methods may be used by a healthcare provider to advise patients of current alternatives, e.g., it updates the ICF to include any developments in management and treatment that would be beneficial or detrimental or that could cause them to choose another course of action. The subject methods and systems can also be part of a patient management method which includes recontacting former patients when new developments occur. The term "duty to recontact" refers to the possible ethical and/or legal obligation of medical or genetic service providers to recontact or attempt to recontact former patients about advances in research that might be relevant to them. Patients' knowledge of advances in the molecular genetic bases of their disorders may have great impact on their lives, affecting their psychological well being, reproductive options, employment decisions, and lifestyle choices such as marriage; in addition, there is a consensus in the medical genetics community that patients should have access to information about such advances. Such recontact of patients may be triggered in the systems and methods described herein upon the occurrence of such situations as (1) those in which a diagnosis had been suspected, but not made, and a new diagnostic test has been developed; (2) those in which a more accurate diagnostic and/or prognostic test, postnatal or prenatal, has been developed (e.g., from linkage to mutation detection); and (3) those in which new information may alter the prognosis or recurrence-risk estimates.

From the perspective of a biomedical professional the systems and methods described herein provide tools that allow for easily identifying human subjects that may be appropriate for a study or action and for contacting these subject with the requests for the required consent. The invention therefore can also be seen as tools that make it easier for a biomedical professional to organize a study or other action.

The invention, in its various embodiments, recognizes and addresses these and other problems and overcomes many limitations encountered by those skilled in the art by bringing together, and bridging the gaps that have existed between the legal, medical, consumer and training fields with respect to establishing dynamic, certifiable informed consent.

Those skilled in the art will appreciate that the subject processes and systems can, but need not, be carried out in a fully or semi-automated manner, e.g., utilizing computer systems to generate the ICFs, archive the executed ICFs, and prompt for recontact of a subject when necessary. For ease of reading, the following description of exemplary embodiments is directed to the utilization of computerized systems for at least certain aspects of the subject process.

Exemplary Embodiment

FIG. 1 depicts a first embodiment of the system according to the invention. Specifically, FIG. 1 depicts a system 10 that allows a plurality of human subjects to control, optionally dynamically, the consent that they grant for the use and access of their medical, genetic and biological data. Additionally, as well be explained in more detail below, the system 10 depicted in FIG. 1 provides a platform that allows a biomedical professional to easily enroll participants into a study or other action. The system 10 depicted in FIG. 1 will now be explained in the context of a system that allows individuals to control dynamically the consent they grant over their data during a process in which the individuals decide whether to enroll within a study being offered by a biomedical professional. However, although FIG. 1 is merely representative of one embodiment of the invention, an embodiment that integrates a plurality of components into a single system. It will be apparent to those of skill in the art that a single integrated system is not required and that the different components of the system may be kept separate from each other and operate a different locations with communication occurring over a data network or through some other methods.

In the embodiment of FIG. 1, the system 10 contemplates a single integrated system of the type that may be maintained and operated by a trusted third party. A trusted third party could include a company, government agency organization or other entity or entities that are familiar with the different relevant legislative frameworks that control and regulate the distribution of medical data, identity data, genetic data, and other types of controlled data. Typically, the trusted third party would be an entity that is also familiar with the rules and regulations that control and regulate the requesting and granting of informed consent. However, it will be apparent to those of skill in the art that the systems and methods described herein may be employed in other contexts, including contexts wherein there is no trusted third party and the entity that is carrying out the enrollment process is the biomedical professional themselves, or an organization supporting the biomedical professionals, such as a pharmaceutical corporation, a hospital, or some other type of entity. However, for the purpose of clarity the system 10 will now be described within the context of an enrollment process that employs a trusted third party for brokering the exchange of a request for consent and the delivery of consent between biomedical professionals and individuals that have stored their data in a data repository.

More particularly, FIG. 1 depicts a system 10 that includes a query process 12, a database 14, a recontact process 18, a portal process 20, a consent process 22, an enrollment request 24, a list of enrolled participants 28 and a query 30. In a typical embodiment, the different processes and the database 14 may be realized as a data processing system comprising a computer program and a computer server on which that program is executing. Accordingly, each of the processes 12, 18, 20 and 22 depicted in FIG. 1 may represent a single computer program that is running on a computer server. Similarly, the depicted database 14 may represent a database management system computer program and a non-volatile storage device or other type of data memory capable of providing long term storage of data. The query process 12 may be a SQL query process of the type commonly employed for performing queries of data stored within a database system.

More specifically, the depicted database 14 may be any suitable database system, including the commercially available Microsoft Access Database, and can be a local or distributed database system. In this embodiment, where a trusted intermediary is employed, the database 14 may be part of a genetic banking system, such as the ENTRUST genetic banking system provided by First Genetic Trust of Chicago 111. Such a genetic banking system can provide secure storage of a person's demographic, medical, genetic, and biological data. As well as other information the person chooses to store. As is described in the above referenced U.S. application Ser. No. 09/939,200, Filed: Aug. 24, 2001, titled METHOD FOR INDEXING AND STORING GENETIC DATA, the database 14 may provide for secure storage of data such that patient identity information is stored separately from patient medical data. As described in the referenced application, each person storing data in the database may be provided with a virtual private identity (VPI) code that links the patient to their identity information. This identity information may kept in a secure and encrypted database. The VPI may also be used as a key into a second separate database that contains inter alai, medical, genetic, biological and sample data. Thus the VPI can act as a link between a person's identity data and their medical data. By controlling the VPI so that it can only be used by a entity authorized by the person (typically by requiring the person to provide a private key to be used with the VPI) the database 14 can allow access to the patient's medical, genetic and biological data, without allowing access to the patient's identity information.

Although the database systems described in the above-identified reference may be employed with the system 10, it will be understood that other database systems may be employed as well. The design and development of suitable database systems are described in McGovern et al., *A Guide To Sybase and SQL Server*, Addison-Wesley (1993), the contents of which are incorporated by reference. The database 14 can be supported by any suitable persistent data memory, such as a hard disk drive, RAID system, tape drive system, floppy diskette, or any other suitable system. The system depicted in FIG. 1 includes a database device 14 that is integrated with the system 10. However, it will be understood by those of ordinary skill in the art that in other embodiments the database device 14 can be separate from and even remotely located from the system 10.

In either case, the system 10 includes within the database 14 a storage location for storing information that is representative of the grant of consent provided by a person. This grant of consent typically includes a grant of informed consent that indicates the type of access and uses that may be made of the person's information. Additionally, the consent data typically includes a field to indicate whether the person has consented to being re-contacted. Further and optionally, the grant of consent may include data representative of restrictions put on the use of the data by the person, where these restrictions or consents relate to whether interested parties, such as researchers, clinicians, pharmaceuticals companies, or others, can search their data or contact the person. Similarly, the consent may include a restriction on the manner in which a person may be re-contacted. For example, the person may require all contacts to be made by a trusted third party, and may require that the contact by sent by e-mail to the person's physician. Thus, it can be seen that the system 10 of the invention now provides the genetic baking system with consent information that may be stored with the person's medical, genetic and other data and that may indicate controls, permissions and restrictions placed on the data by the user.

How the medical data and consent data get stored or organized within the database 14 will depend upon the application and any suitable technique may be employed. The organization of data within the database system 14 will, typically, involve a set of tables and fields that will organize the data into searchable units. This table and field structure is described in the above-cited McGovern reference.

With consent data now stored in the database 14, a query process, such as the query process 14 may be provided that checks with the consent data when performing searches for a bio-medical professional—or an intermediary acting at the request of a biomedical professional. The query process 12 can generate queries that act on the tables and fields of the database 14 for the purpose of being able to sort through data that is stored in the database 14. The query process 12 also organizes data into search results that will be returned as the response to the query 30. Accordingly, an authorized biomedical professional that may have logged onto the system 10 via a secure Internet session may submit a query 30 to the query process 12, and the query process 12 can analyze that query 30 and create an SQL compliant demand that may be understood by the database 14. In a typical example, the query 30 submitted by the biomedical professional will be a request to search through the data tables of database 14 to identify medical, biological, genetic or phenotype data having certain characteristics.

The query 30 may include other parameters as well including demographic parameters and medical history parameters. In any case, the query 30 submitted by the biomedical professional will be processed by the query process 12. The query process 12 will determine a set of SQL commands that may be used to identify the set of data that satisfies the parameters outlined within the query 30. The depicted query process 12 will also review the consent data associated with any information that meets the parameters of the search query 30. To this end, in one embodiment, the query process 12 develops SQL commands that retrieve from the database 14 a set of identifiers that represent individuals that have stored data relevant to the query 30. The identifiers are often anonymous in that they themselves lack identifying information—such as the VPIs described above. The identifiers are returned for persons that have stored data that meet the requirements of the query 30. The query process 12 can then review the identified consent data and determine which of the individuals have provided an associated grant of consent with their data that indicates consent to be re-contacted. The re-contact consent is often for the purpose of receiving requests to change the grant of consent they earlier provided. The query process 12 may then forward to the recontact process 18 the list of individuals that meet the parameters set up in the query 30 and that have agreed to be re-contacted.

As described above, the type of restrictions, permission and access controls provided by the person within their consent data may vary according to the application. Consequently, the query process 12 may perform other operations. For example, in those applications where people are allowed to restrict whether their data or portions of their data can be searched, the query process 12 may perform an initial process that identifies which data records or portions of data records stored in database 14 may be processed. In other embodiments, where people are allowed to restrict what types of entities can search their data, such as only allowing trusted parties or bio-medical professionals associated with research hospitals carrying out studies on a particular form of cancer, the query process 12 may first do an initial sort of the data records to identify data that is available for searching under these parameters.

In an optional embodiment, the query process 12, or another process, may also include an authorization process that requires a biomedical professional to enter a user name and password into the system. The user name and password can associate the biomedical professional with the particular entity, or type of entity, project, or type of research. In this embodiment, the query process 12 can employ information about the biomedical professional to determine whether the biomedical professional has been granted the right to search data within the database 14. In some embodiments, the database 14 may be subdivided into different sections, with certain sections of the database being available to biomedical professionals of a particular type, such as academic researchers or researchers conducting studies related to a particular type of cancer. Thus in these embodiments, the query process 12 may limit the application of query 30 to that data which has been authorized to be searched by biomedical professionals of the identified type.

In further optional embodiments, the query process 12 may include a decryption process that can decrypt data that has been stored in an encrypted format. For example, in one embodiment all data stored in the database 14 is stored in an encrypted format. The decryption process may employ a password based encryption/decryption algorithm that can encrypt and decrypt stored data as a function of a password employed by the database 14. Processes for encrypting data can include simple XOR algorithms, one-time pad based algorithms or more complex ciphers including any of the algorithms or techniques described in Bruce Schneir, *Applied Crytpography* (Addison-Wesley 1996), the contents of which is herein incorporated by reference. Any of these processes may be carried out by the query process 12, and other process shown in FIG. 1, to allow these process to manipulate in clear text data that has been stored in an encrypted format.

In either case, the depicted query process 12 can return a list of individuals that have medical, genetic and other data that meet the parameters of the query 30 and that have agreed to be re-contacted. In one embodiment, the query process 12 provides the search results to the biomedical researcher. The search results in one practice include the relevant medical data and the consent data granted for the medical data. Depending upon the application, the system 10 may default to a process that requires that each person providing data be re-contacted with a request to execute a new grant of consent. This is the process that is implemented by the system 10 of FIG. 1. In an alternate practice, the system 10 may allow the bio-medical professional, or some other entity to determine which of the individuals are to be re-contacted. Other practices may be employed depending upon the application at hand.

In either case, the re-contact process will be invoked. In the depicted embodiment, the re-contact process 18 responds to the request of the query process 12 to recontact each of the identified individuals. To this end, the recontact process 18 can obtain or generate information that may be helpful to an individual that is going to be recontacted with a request to change their granted consent. In one embodiment, the recontact process 18 requests the biomedical professional to provide a brief description of the purpose of the study or other action being proposed. Additionally, the recontact process 18, as will be described in greater detail hereinafter, may require the biomedical professional to go through an informed consent process that generates, by itself or as part of a larger process, an appropriate and compliant informed consent form that may be provided to the different individuals that are going to be re-contacted. One process for generating such an informed consent is shown in FIGS. 2A-7.

Once the recontact process 18 has the necessary information to request the individuals to consider changing their grant of consent, the process 18 can send a request to the portal process 20. In one embodiment, the portal process 20 includes an HTTP compliant server process that provides a secure portal that allows individuals storing data in database 14 to access an account maintained used by the system 10. The portal process 20 notifies the individuals of a request for them to consider joining a study, procedure, or some other activity that requires the individual to change the grant of informed consent.

In the depicted embodiment the portal process 20 accesses the database 14 for each individual identified by the recontact process 18. For each individual, the portal process 20 retrieves from database 14 a patient code that may be employed for generating an enrollment request page that will be served by the portal process 20 to the respective individual when that individual next logs onto the portal. Additionally, and optionally, the portal process 20 may retrieve from the database 14 a contact data record that provides some kind of addressing information so that the portal process 20 may proactively notify the respective individuals that there is a request for them to consider altering their grant of informed consent. In one practice, the portal process 20 retrieves contact data that is representative of an email address. The portal process 20 can then email to the individual a request that they visit the secure portal site to view the information that has been generated by the recontact process 18 and which will be served by the portal process 20 once the individual accesses the secure portal. Once the individual has accessed the portal, the portal process 20 can present the enrollment request 24, which may be a typical web page, to the individual. If the individual so chooses, in this embodiment they may activate a link provided on the enrollment request page that returns to the portal process 20 an indication that the individual has agreed to the change of informed consent. To this end, the portal process 20 can activate a consent process 22 that updates the granted informed consent information stored for that individual within the database 14. The processes for updating the informed consent data record can vary and examples of such processes are depicted in FIGS. 9-13.

Thus, it will be understood that the portal process 20 can also be understood as on example of a consent process that will be employed by the system for allowing a person to change the grant of consent provided with their data and stored in the database 14. Other examples of consent processes are set out below with reference to FIGS. 9-13.

In depicted embodiment, each time an individual changes their consent within the database 14 the recontact process may be notified. If the recontact process 18 determines that the individual changing their consent is associated with the list generated by query process 12, the recontact process 18 can indicate that the individual has enrolled within the associated study and, optionally after a set period of time, generate a web page 28 of enrolled participants. The web page 28 may be served over a secure connection to the associated biomedical professional.

Accordingly, FIG. 1 depicts one exemplary system according to the invention that allows individuals to agree to change the grant of informed consent such that the individuals may participate in a study or action that may be of benefit to them.

Figure 2A:
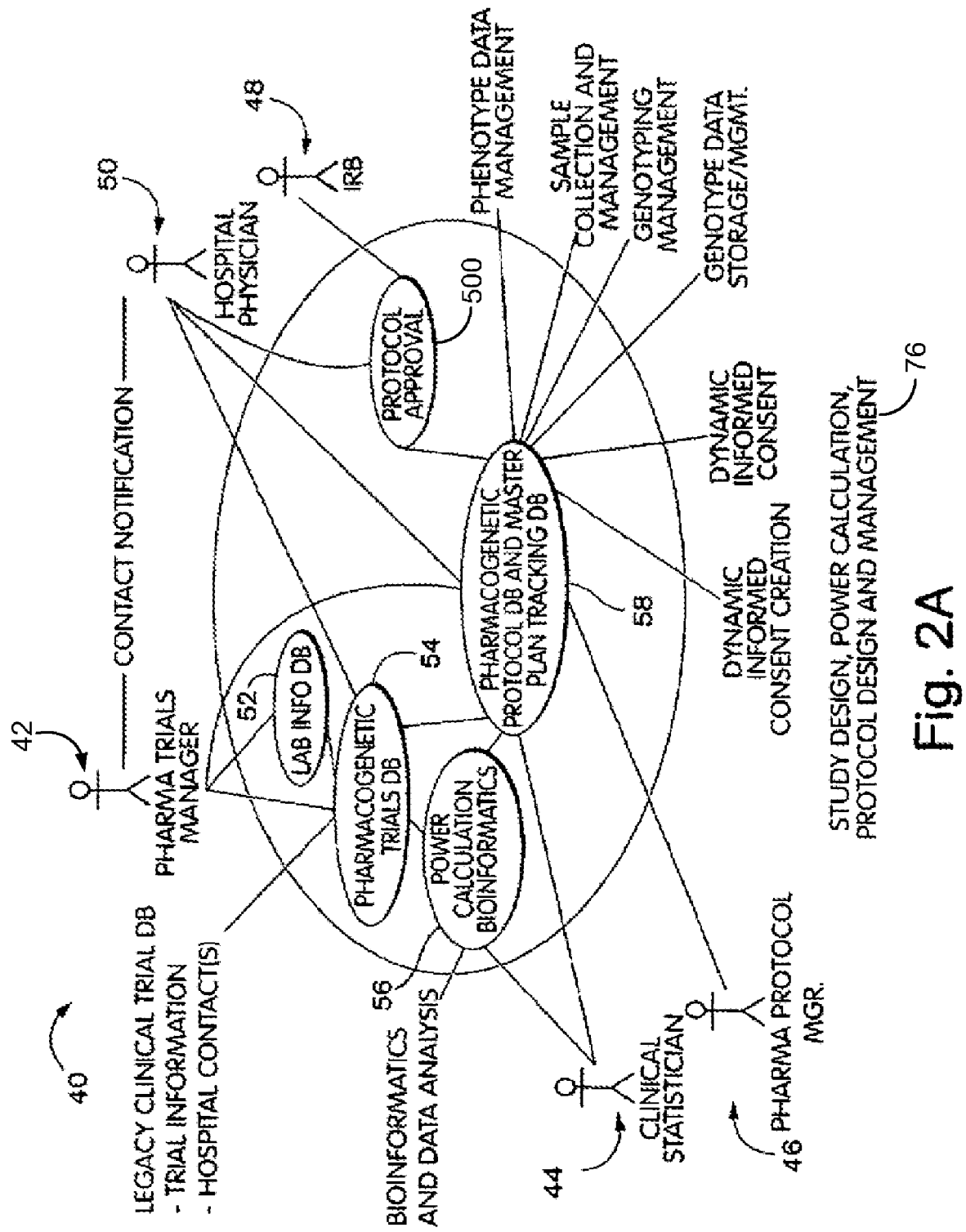
FIG. 2A depicts a process of compiling together study-specific (i) ICFs, and (ii) genetic education.
Figure 2B:
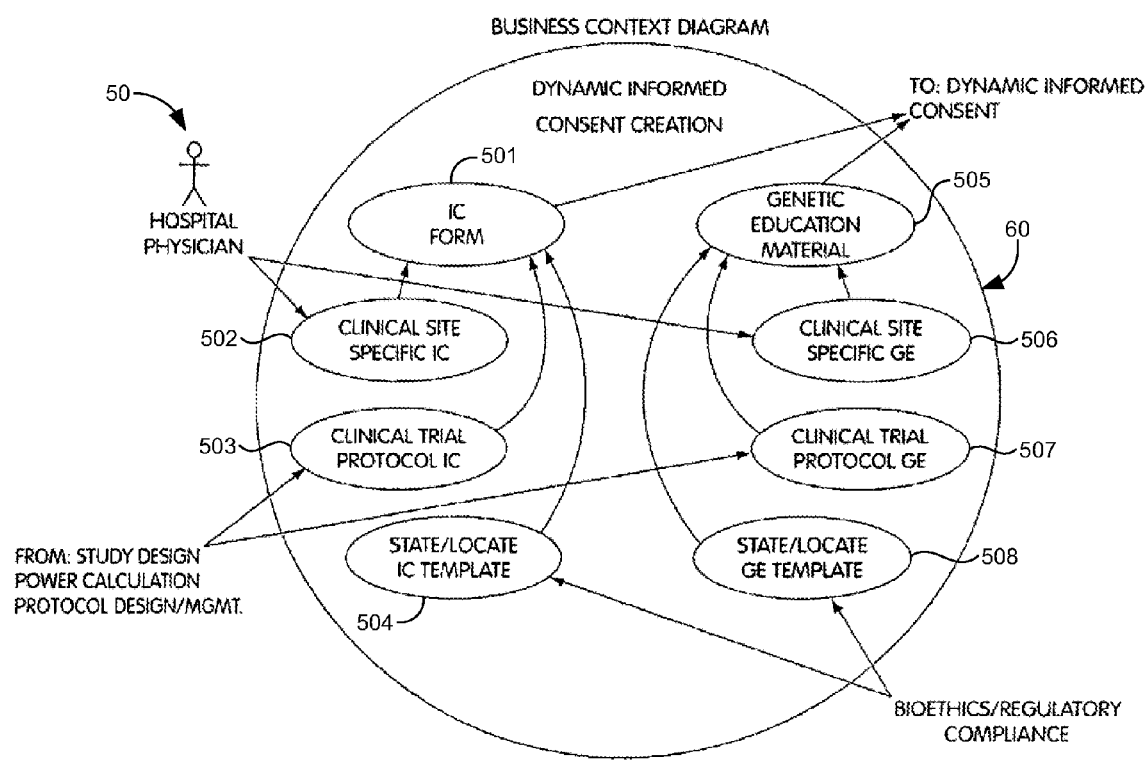
FIG. 2B depicts a process of compiling together study-specific (i) ICFs, and (ii) genetic education.

In the system 10, each time the biomedical professional wants to re-contact a human subject, the biomedical professional provides the system 10 with an informed consent form that the human subject is to review and execute. The informed consent form (ICF) may be manually prepared by the biomedical professional. However, in certain alternative embodiments, the ICFs are created in an automatic or a semi-automatic way. Typically, every action or study has a number of predefined associated sites (in the case of pharmacogenetic trials, the sites are the participating hospitals). The system 10 can assemble and maintain a database of regulation-compliant ICF templates for some or all possible sites. When the protocol for the study has been finalized, the Manager of the study requests the generation of appropriate ICFs for all participating sites. As FIGS. 2A and 2B illustrate, this request can start an automatic process which:

1. Generates appropriate ICF templates for every participating site (e.g., all such sites that have registered on the DICP system during the process of setting up the study). Appropriate sections of the templates can be automatically filled by information extracted from corresponding sections of the study protocol.

2. Notifies the Protocol Manager of the study to fill in those sections of the ICF templates which were not handled automatically in the previous step.

3. Forward the generated ICFs for internal review and then for review, comments and IRB approval to the appropriate contact persons at the participating sites. The contact persons may get back to the Protocol Manager with requests for modifications, made by the IRB at the contact persons' sites.

Particularly, FIGS. 2A and 2B depict pictorially a process for designing a study, such as the study of the efficacy of a cancer drug, as well as a process for developing a protocol design and study management. Thus, FIGS. 2A and 2B describe how a study and protocol may be designed and managed and it will be understood that the created study and protocol may be implemented by employing the systems and methods described herein including the system 10 depicted in FIG. 1.

Turning to FIG. 2A, the major actors involved in study design, power calculation, protocol design and management are depicted. Specifically, FIG. 2A depicts a study design process 40 wherein a pharmaceutical trials manager 42, a clinical statistician 44, a pharmaceutical protocol manager 46, an internal review board agent 48, and a hospital physician 50 come together and cooperate to develop a study. As depicted in FIG. 2A, the pharmaceutical trial manager 42 can help determine the type of lab information that will need to be collected and data based for the study as well as the different pharmacogenetic information that will have to be collected and then stored as well. As shown in FIG. 40, the pharmaceutical trial manager 42 can help develop the lab information database 52 as well as the pharmacogenetic trial database 54. In practice, legacy clinical trial databases may be employed to help supplement or seed these databases. Information on these databases can include trial information from past legacy clinical trials and hospital contact information. Other information may be stored in these databases 52 to 54 as well.

FIG. 2A further depicts the clinical statistician 44 may contribute information to a type of bio-informatic database 56 and may help determine the type of information that needs to be stored in this database 56. Additionally, the clinical statistician 44 may help design the pharmacogenetic protocol database and master plan tracking database 58 that will be employed during the study. As further shown in FIG. 2A, the pharmaceutical protocol manager 46 may aid in the development of the pharmacogenetic protocol database 58 as well. The depicted hospital physician 50 may communicate with the pharmaceutical trial manager 42 and may provide input to the various databases including the pharmacogenetic database 54 and the pharmacogenetic protocol database 58. Additionally, as shown in FIG. 2A, the hospital physician 50 may participate in the protocol approval process 500 along with the internal review board agent 48. The information collected during the study design can include information regarding phenotype data management, sample collection and management, genotyping management, genotype data storage and management, as well as information about the dynamic informed consent that will be necessary and information that may be employed for dynamic informed consent creation. Thus the database can store information about the required informed consent as well as information that can help the system 10, optionally, dynamically generate the informed consent that will be provided to human subjects.

FIG. 2B depicts pictorially the kinds of information that may, representatively, be employed during the dynamic informed consent creation process. Specifically, FIG. 2B depicts a process 60 that shows different factors considered during the dynamic informed consent creation process. These factors can include the type of information normally provided by an informed consent form 501, specific informed consent information for the clinical site 502 as well as protocol informed consent information for the clinical trial 503 and templates of informed consent forms that comply with state, local, and federal guidelines and regulations 504. FIG. 2B further depicts that optionally genetic education material 505 may be provided as part of the dynamic informed consent. Additionally, genetic education material that is relevant to the clinical site 506 as well as the clinical trial protocol 507 and different state, local, and federal regulations 508 may also be part of the process that dynamically generates the informed consent form.

Figure 9:
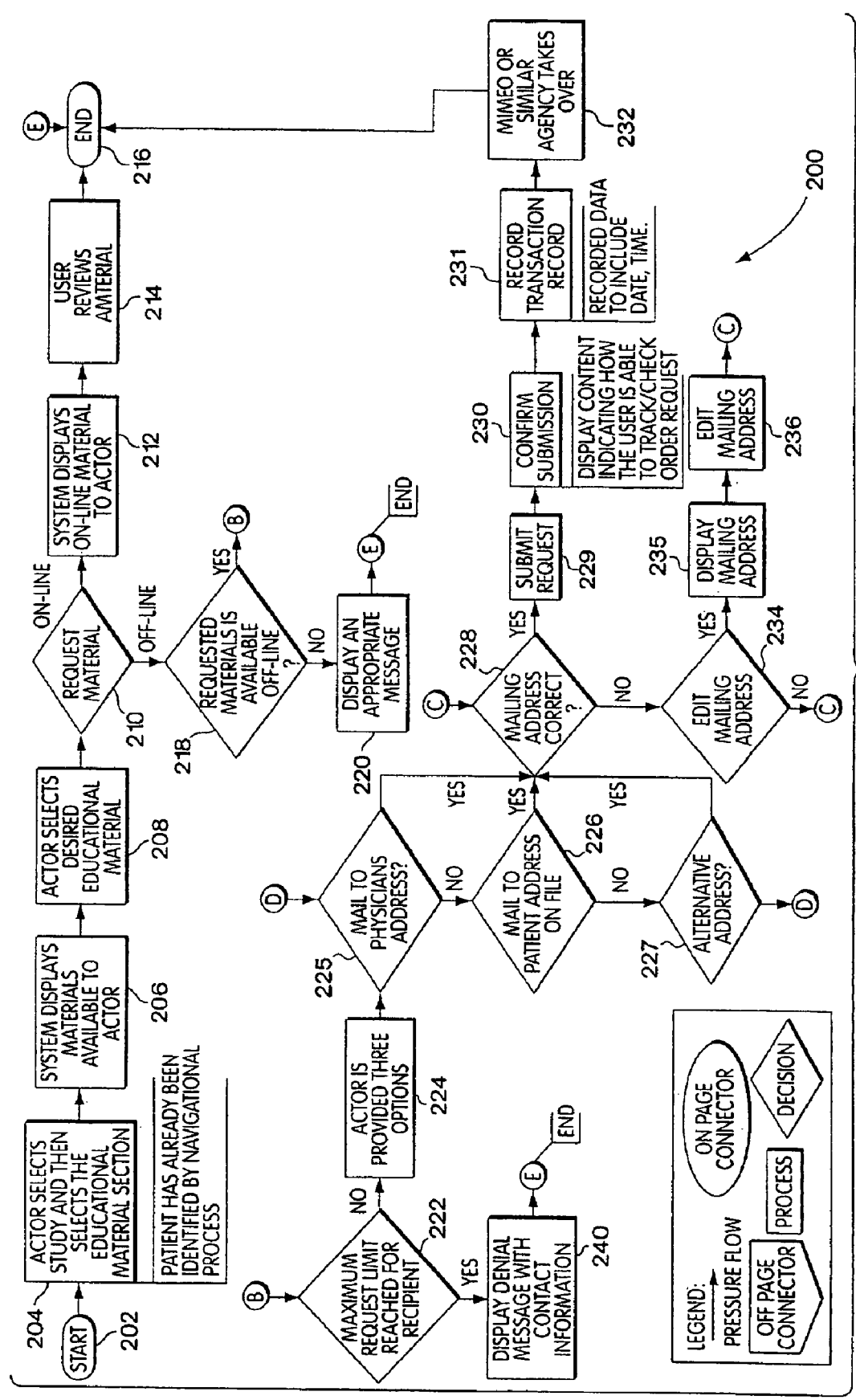
FIG. 9 depicts a process for managing requests for on-line and off-line educational materials.

Optionally, other educational material may be assembled together with the 1C form. This can be a content building process, where both on-line and off-line educational material for a specific study is compiled. Off-line educational material can include books, videos, CDs etc. As in the compilation of the 1C forms, there are multi-language issues and educational templates that are specific to individual locales and study. Further, each Human Subject may include with their demographic data a preference of language selection. This preference of language selection may be employed by the ICF process to generate a form and select templates written in the selected language. FIG. 9 depicts one process for providing educational materials to the Human Subject. The language of the educational materials may similarly be selected according to data stored in association with the person receiving the educational material.

Figure 3:
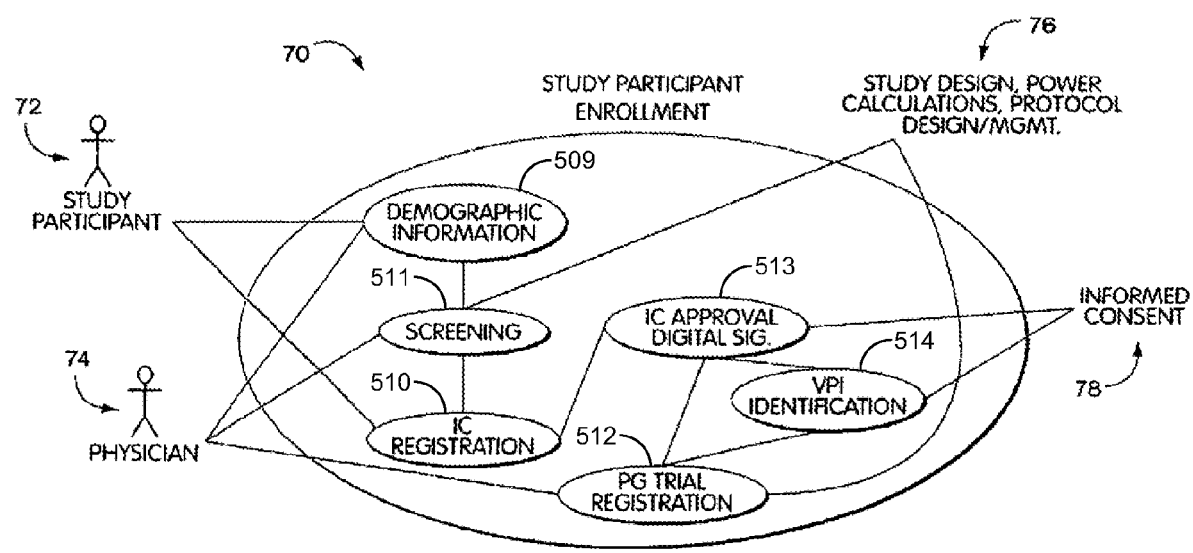
FIG. 3 depicts a process of enrolling participants in a clinical study.

As shown in FIG. 3, the enrollment of an individual X in a study can be performed by an authorized Person Y (usually a Physician participating in the study). In particular, FIG. 3 depicts a study participant enrollment process 70. In particular, FIG. 3 depicts pictorially that a study participant 72 may provide demographic information 509 and may complete the necessary informed consent 510 to register for the process. Optionally, a physician 74 may look at the demographic information as well as various screening criteria 511 to determine whether the study participant should be enrolled in the process. The screening criteria as well as the trial registration process 512 may be performed according to the study design and protocol design and management guidelines 76 that were developed during the process 40 depicted in FIG. 2A. FIG. 3 further depicts that the informed consent 78 provided by the study participant 72 may be, in some optional embodiments, provided electronically by the study participant 72 employing a digital signature 513 to execute the dynamically generated informed consent form. In the process 70 of FIG. 3 a virtual private index identification code 514 is provided to the study participant 72. This code may be employed by the study participant to allow the study participant to provide medical, biological, genetic or phenotypic data to the study but do so using the VPI so that providing the information is done anonymously. The VPI provided to the study participant 72 may be employed by the study participant 72 to monitor the study and the optionally receive information from the physician 74 conducting the study. One technique for generating VPI codes is described in the above referenced U.S. Patent Application entitled METHOD FOR INDEXING AND STORING GENETIC DATA.

The exemplary enrollment process may involve the following steps:

1. Screening: the authorized Person Y performing the enrollment should confirm that the potential Study Participant X meets the requirements for being part of the study. To do so, Y may log onto the DICP system and get access to that part of the protocol of the study that defines the inclusion/exclusion requirements that study participants are to meet.

2. Registration/Certification: If X is not already in the database, then Y may register X with DICP. This step involves, for example, entering the personal information of X into the system, and requesting credentials for X (such as user Id and password or/and the creation of a digital certificate). The outcome of this step is to make X a "registered person" in the DICP system.

3. Account Creation/Update: If X has never before participated in a DICP study, a new Login Account can be created; otherwise, his or her existing Account is used. The Login Account is updated with the addition of an entry for the study at hand. This entry is automatically populated with links to on-line educational material for the instant study, links to the on-line informed consent documents, etc.

Figure 4A:
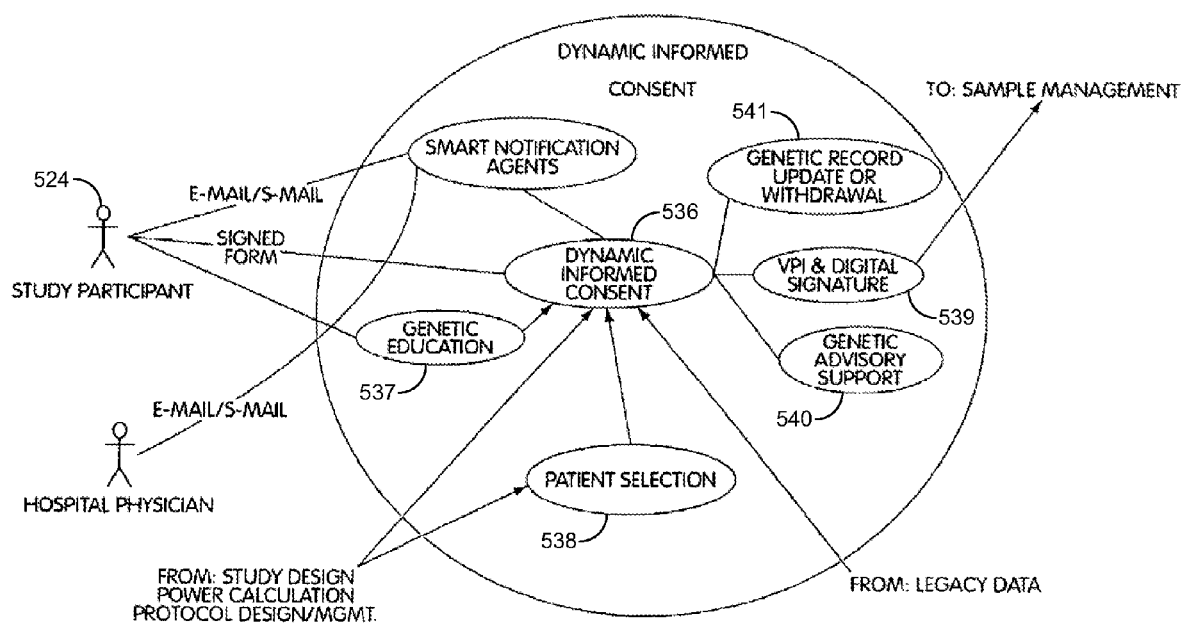
FIGS. 4A and 4B depicts a process whereby a study participant may manage some portion of his or her Informed Consent forms.

There are a number of occasions where it may be advantageous to permit a Study Participant to manage at least a portion of his of her informed consent process. FIG. 4A illustrates certain embodiments whereby the Study Participant 524 participates in managing at least a portion of the process involved in complying with informed consent requirements for a study.

In general, before participation in a study begins, a Study Participant 524 is selected 538 and must sign 539 the appropriate ICF or ICFs 536 for the study, e.g., after receiving the appropriate study-specific education/counseling 537. In the illustrated embodiments, at the time of the Participant's 524 enrollment, on-line educational material 540 and on-line ICFs are linked to the Participant's Account 541 (as part of the Account entry created for the study at hand). In such embodiments, the subject system may include an educational material system that allows an account holder (or an authorized user typically a study participant or prospective participant) to gain access to educational material both on-line as well as by physical delivery of offline educational materials for any of the studies he is participating in. The physical delivery can be, e.g., by mail or may be outsourced to a third party vendor. In certain embodiments Study Participants (or authorized Proxies) may also be able to access on-line or off-line counseling through their account, such as genetic counseling.

Figure 5:
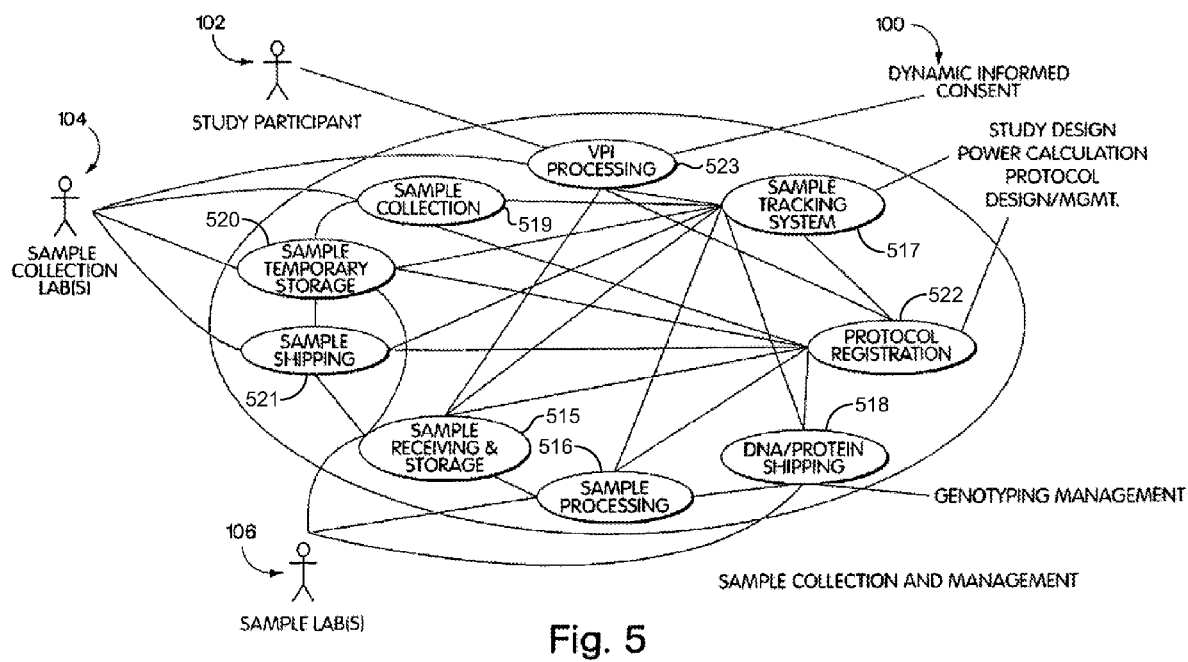
FIG. 5 depicts a process for sample handling and collection.

Accordingly, FIG. 5 depicts pictorially a process 100 wherein a study participant 102 that is provided by an identity code, in this case, a virtual private identity (VPI) code 523, provides biological, genetic, or some other sample data to the study. The process 100 provides a sample collection and management protocol process that allows samples to be collected 519, temporarily stored 520, and shipped 521. The protocol further provides for sample receiving and storage 515, sample processing 516, sample tracking 517, and DNA and protein shipping 518. The different steps in the sample collection and management can be carried out in accordance with the protocol. The set up for these processes is set out by the protocol registration 522. In the process 100 depicted in FIG. 5 the study participant may give informed consent to the use of their sample data. However, once the data has been sampled and stored and information about that sample has been stored in the database 14, the data are, if authorized, available to consider for use in subsequent studies. Accordingly, the system 10 depicted in FIG. 1 provides a DICP system that a biomedical professional may employ for contacting enrolled participants and distributing to them new informed consent forms that follow the guidelines and requirements set up for the proposed study and provide the necessary level of consent or grant of consent to conduct the study. Thus, in this example, samples that were originally were provided by the study participant for one particular sample of processing procedure may subsequently be of interest to a biomedical professional for another study. In this situation, the study participant 102 may be recontacted by the DICP system 10 with a new informed consent form and a request that the study participant 102 execute that form so that the storage sample may be employed.

Figure 12:
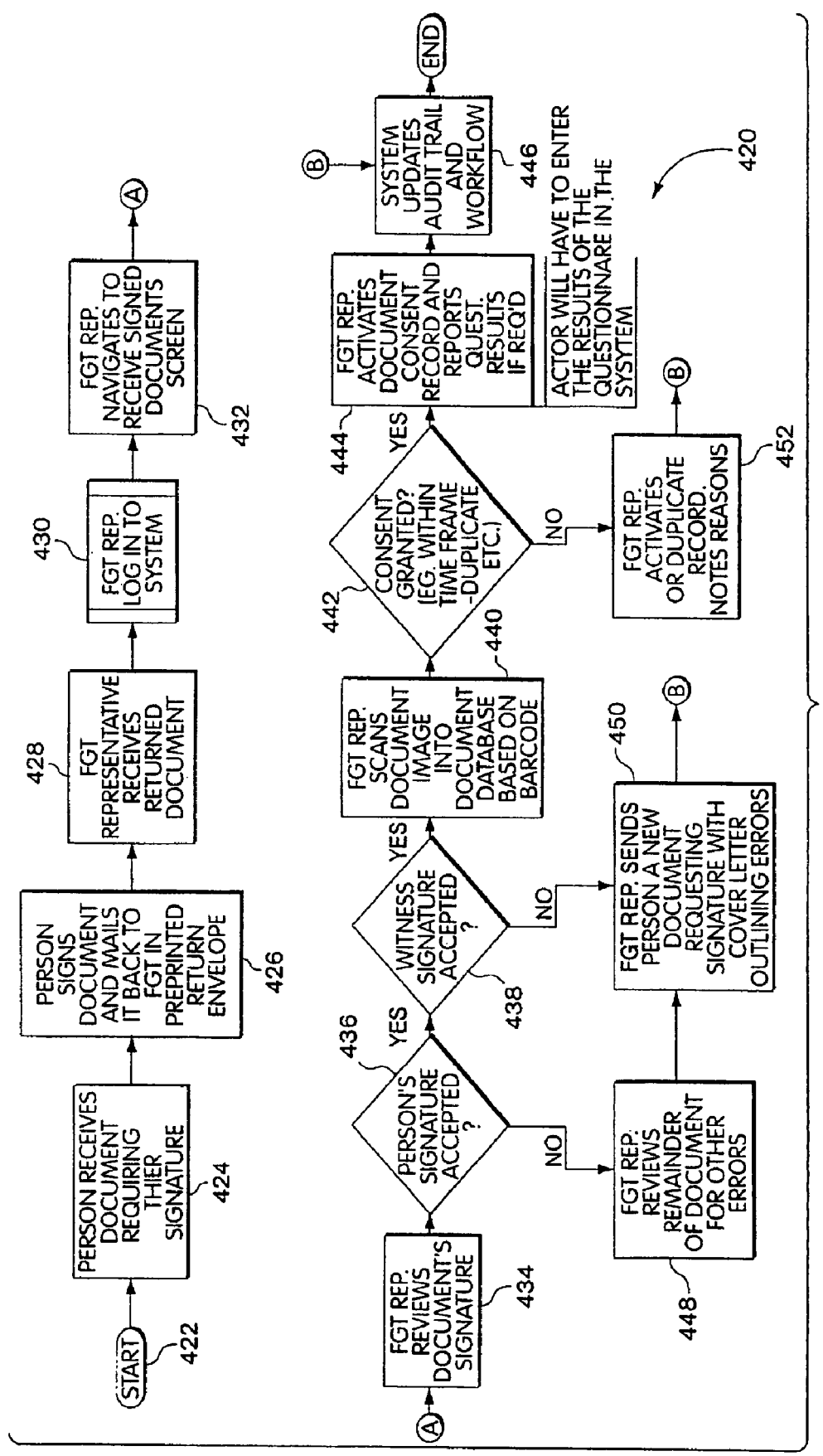
FIG. 12 depicts a process for managing hard copies of executed ICFs.

Whether the ICF is generated dynamically or not, the ICF is delivered and signing of the ICF can be performed either on-line or off-line. As FIG. 12 shows, in certain embodiments, the Participant can print out a copy of the ICF, sign the document, and return the signed document to the DICP system 10. In certain preferred embodiments, an image of at least the signature page(s) is captured and the audit trail for that Participant is updated. To facilitate tracking of such documents, a bar code can be generated on the documents at the time they are printed. Upon imaging the documents, the bar code can than be used to link the image, or an OCR thereof, with the Account Holder.

Figure 11A:
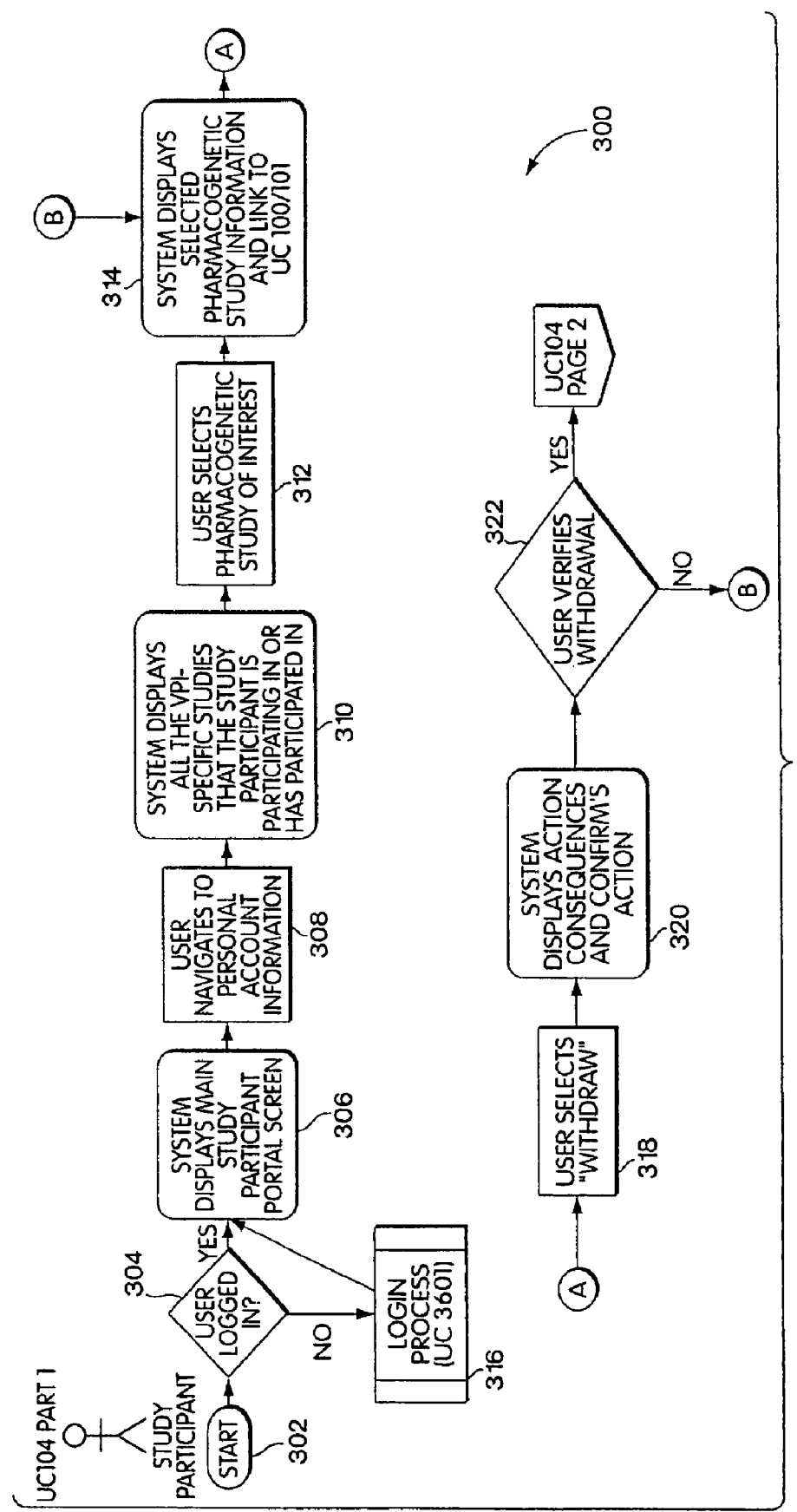
FIGS. 11A-C depict a process for a participant withdrawing from a study.

In certain instances, a study participant may decide to withdraw from a study and request that all the samples taken from him or her in the context of that study be destroyed and all information connecting the Participant to the study erased from DICP system 10. This function allows study participants enrolled in a pharmacogenetic study, as an illustration, to withdraw from the study and request the destruction of all the samples and data taken from him or her in the context of this study. Because study participants may withdraw at various points of a study, there are different dependencies and actions that may occur. Also, the fact that a user withdrawing from one study does not mean he or she is withdrawing from all studies or withdrawing from the DICP system 10. FIGS. 11A, B and C show an exemplary mechanism by which the system can achieve such a withdrawal.

After the study participant has indicated withdrawal from a particular study, the system 10 operates as an ICF manager that may confirm that the participant does indeed want to withdraw. Upon confirmation, the ICF manager will initiate the steps of withdrawal, which optionally includes destruction of the patient's samples and information related to the specific study.

The system 10 has been described as part of an enrollment process for identifying and enrolling human subjects into a study, action or procedure. However, the system 10 may also be seen to provide a system that dynamically creates and/or distributes ICF forms for participants registered with the system 10. Such a dynamic system, that can determine whether there is authorization/consent provided to recontact the human subject and, if authorized, recontact the human subject to get a new grant of informed consent, may be employed in many other applications. For example, FIG. 5 illustrates a sample collection and management protocol. In certain embodiments, the subject DICP 10 system may include a component which provides centralized management, tracking, and auditing of samples obtained from Study Participants, e.g., tissue or cells samples, nucleic acid sequences or the like, and the protocols applied to them. In many instances, such samples may be stored at remote, third-party sample labs. In such instances, the subject DICP system 10 can be used to track operations and events relative to each sample.

Figure 4B:
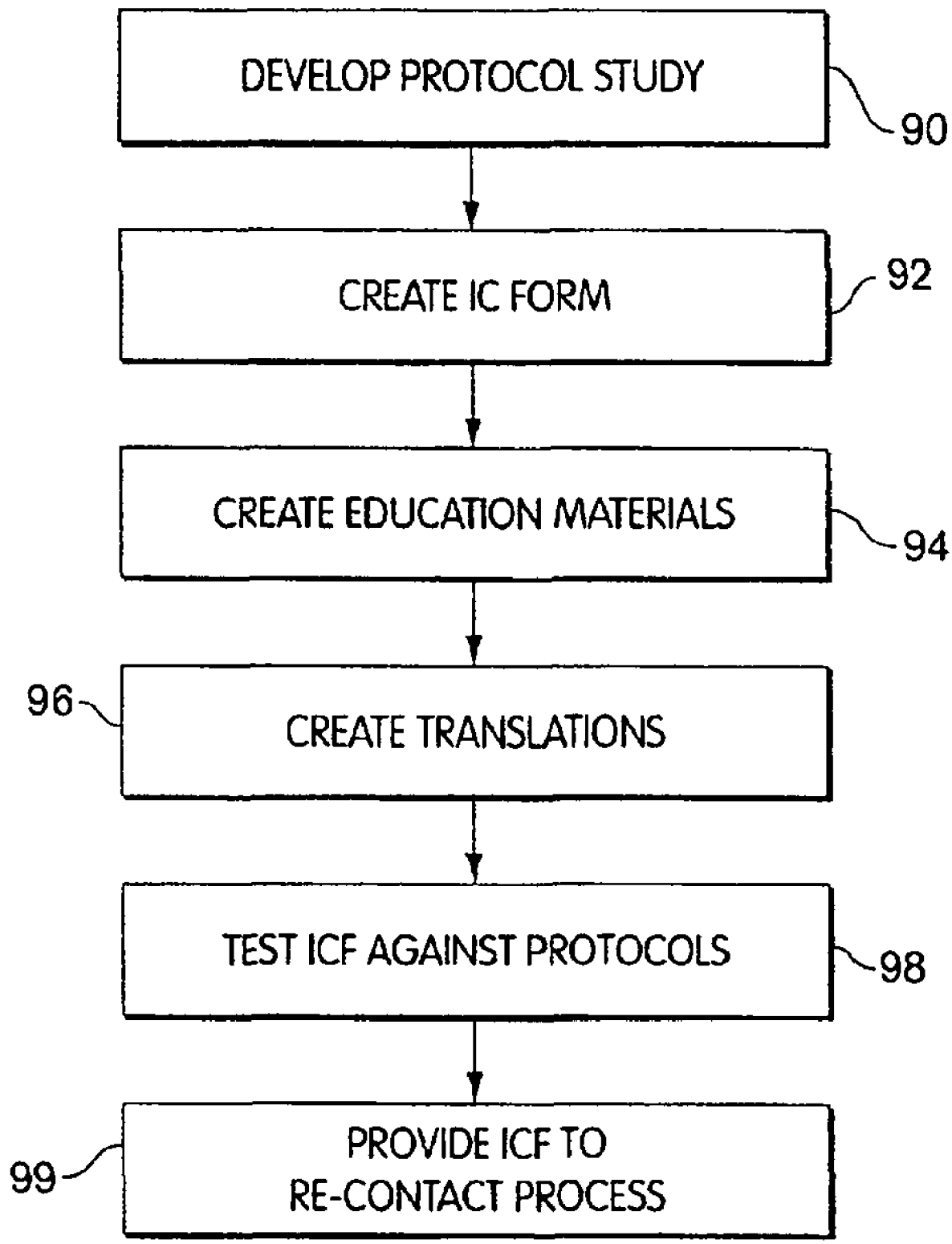

Thus will be seen from the above description that the systems and methods described herein include systems that can optionally dynamically generate an informed consent form that may be employed by the system 10 to enroll a human subject as a participant in a study, action, or other procedure. This process, as described above and as depicted in FIG. 4B, may be realized as a computer program operating on a computer server. As shown in FIG. 4B, the process may include a first step 90 wherein a protocol and study are developed. As described above the development of the protocol and study may be done according to conventional processes that consider the information that needs to be collected before the study, the type of patients that need to be enrolled in the study, the types of protocol that need to be in place for managing information, data, samples, and other elements of the study and review procedures that are to be followed while conducting the study, working with human subjects, and during later data analysis.

As shown in FIG. 4B the process may then move to step 92 wherein the process 90 may create an informed consent form. In step 92 the process 90 may create a template that includes in the template the kind of information that is to be provided to a subject to satisfy informed consent requirements set out by the clinical site, the clinical trial protocol, state, local and federal regulations, and any other criteria that need to be considered under the developed protocol and study. Optionally, the template generated may be an XML form that may include identified fields that contain information that is to be presented to the human subject and fields that are to be completed by the human subject. Fields provided by the human subject may include fields that indicate the type of informed consent being provided by the human subject. For example, the informed consent form may be an XML page that may include fields that may be included by the human subject to indicate whether or not they are willing to be recontacted, what type of researcher, clinician, or entity may recontact them, whether their information and data stored within the database 14 may be viewed, queried, or otherwise employed by interested parties conducting different kinds of research. What kinds of studies they are willing to be contacted about, for example studies related to treatment of cancer, infertility, aids, or some other kind of study.

After step 92 the process may proceed to optional step 94. In optional step 94 the process may create educational materials such as educational materials about genetic education, the disease being treated, or some other relevant educational material. The educational material selected may be chosen to comply with the study protocol and design and to comply with educational requirements set out by the clinical site, the clinical trial protocol, or vary state, local or federal regulations. Other types of educational material may also be provided as part of the informed consent procedure.

After step 94 the process proceeds to step 96. Step 96 is an optional process wherein language translations of the informed consent forms may be generated. Thus informed consent forms may be translated form Spanish to English, from English to Japanese, or into some other language that may be relevant to the pool of perspective participants. The translation of the forms may occur in part or in whole by automatic translation processes. Such automatic translation processes are known in the art and any suitable automatic translation process may be practice with the invention described herein. In particular, automatic translation processes may be employed for processing headings, titles, and instructions that appear within the informed consent form. Optionally, the content provided on the form may be translated by a human translator and entered into the database separately.

When translations are created the process may proceed to step 98 wherein the developed informed consent form is tested against the protocols earlier designed and developed. This step may be an interim step that forwards the generated form to a internal review board or other relevant authority that reviews the form for compliance with the protocols, regulations, and objectives earlier set out. Once the form is approved the process may proceed to step 99 wherein the approved informed consent form is provided to the system 10 depicted in FIG. 1 for subsequent delivery to the appropriate human subjects.

In preferred embodiments, the system 10 is understood as a DCIP system that can also provide support for all the steps that comprise the life cycle of a sample. For instance, the DICP system 10 can be used to track sample acquisition. For instance, to take a sample, an appropriate "sampling protocol" will often be followed. The sampling protocol (e.g., which is part of the study protocol) describes such steps and requirements as (i) how much sample needs to be taken, (ii) how the sample taken needs to be aliquoted (e.g., how many sub-samples should be obtained from the master sample), (iii) procedures for temporary storage of the sample, (iv) procedures for shipping the sample to its final storage destination, etc. When visiting a sampling facility, a Study Participant uses DICP-issued credentials to instruct the sampling facility of the sampling protocol that must be used for that Participant.

To further illustrate, storing a sample may require following the appropriate "sample storage protocol" which defines sample pre-storage handling procedures and appropriate storage conditions (the storage protocol is also part of the larger, study protocol). This protocol is made available to the sample storage facility. For tracking purposes, a sample can be bar-coded or otherwise marked with a study related Sample Id (SID) as well as with a Sample Lab Id (SLID). SIDs are defined in the study protocol and are the means of identifying samples for study purposes. SLIDs are examples of a mechanism that the sample storage facility can use for tracking inventory. In the illustrated example, the link between SID and SLID must be made known to the DICP system 10, in order to allow for appropriate sample tracking.

Samples can be retrieved for a number of reasons, e.g., in order to be sent to a genotyping lab for further processing or in order to be destroyed as the result of a Study Participant's decision to withdraw from the study. In such cases, the procedure to be followed for the retrieval is described as part of the study protocol and should be made available to the sample storage facility.

In certain embodiments, the DICP system 10 compiles and maintains a database of "Sampling Labs" and "Sample Storage Labs". Every entry in this database contains information about the capabilities of that Lab, e.g., which sampling/storage protocols that facility supports. See, for example, FIG. 13. The contents of this database can allow the designer(s) of a study to make educated selection of the sites that will participate in the study, based on the availability of close-by Labs that can support the needs of the study.

Figure 6:
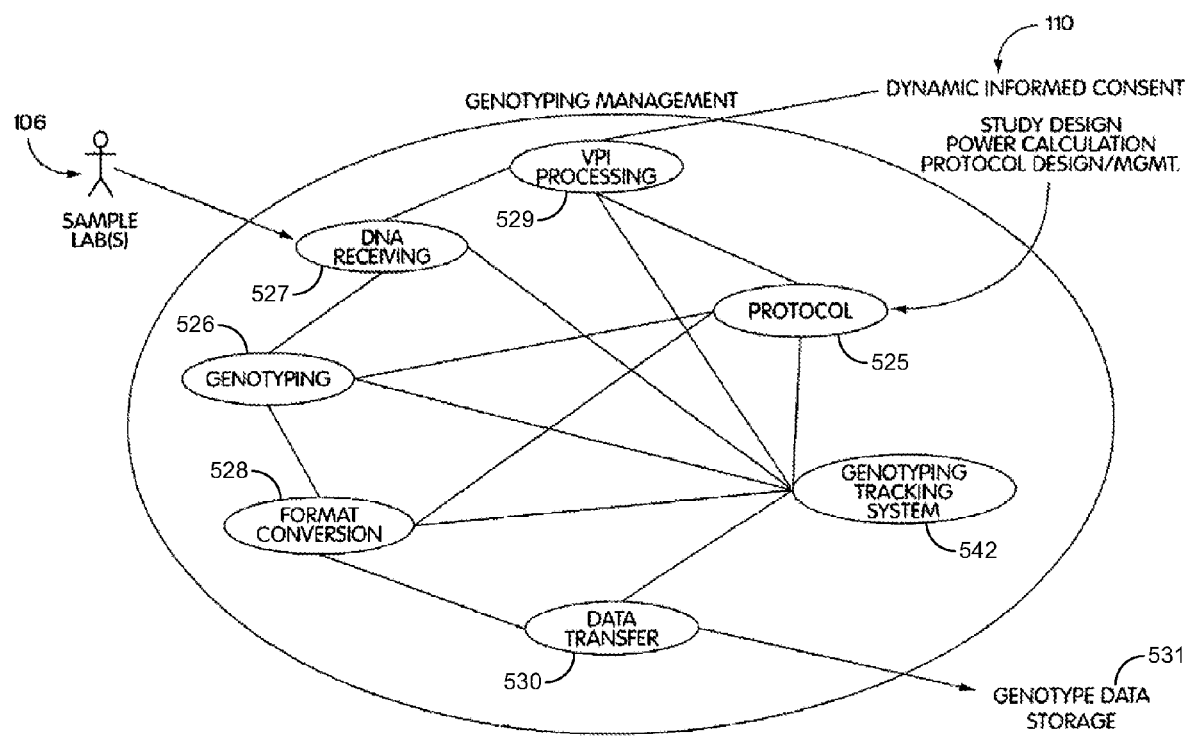
FIG. 6 depicts a process for managing sample genotype data.
Figure 7:
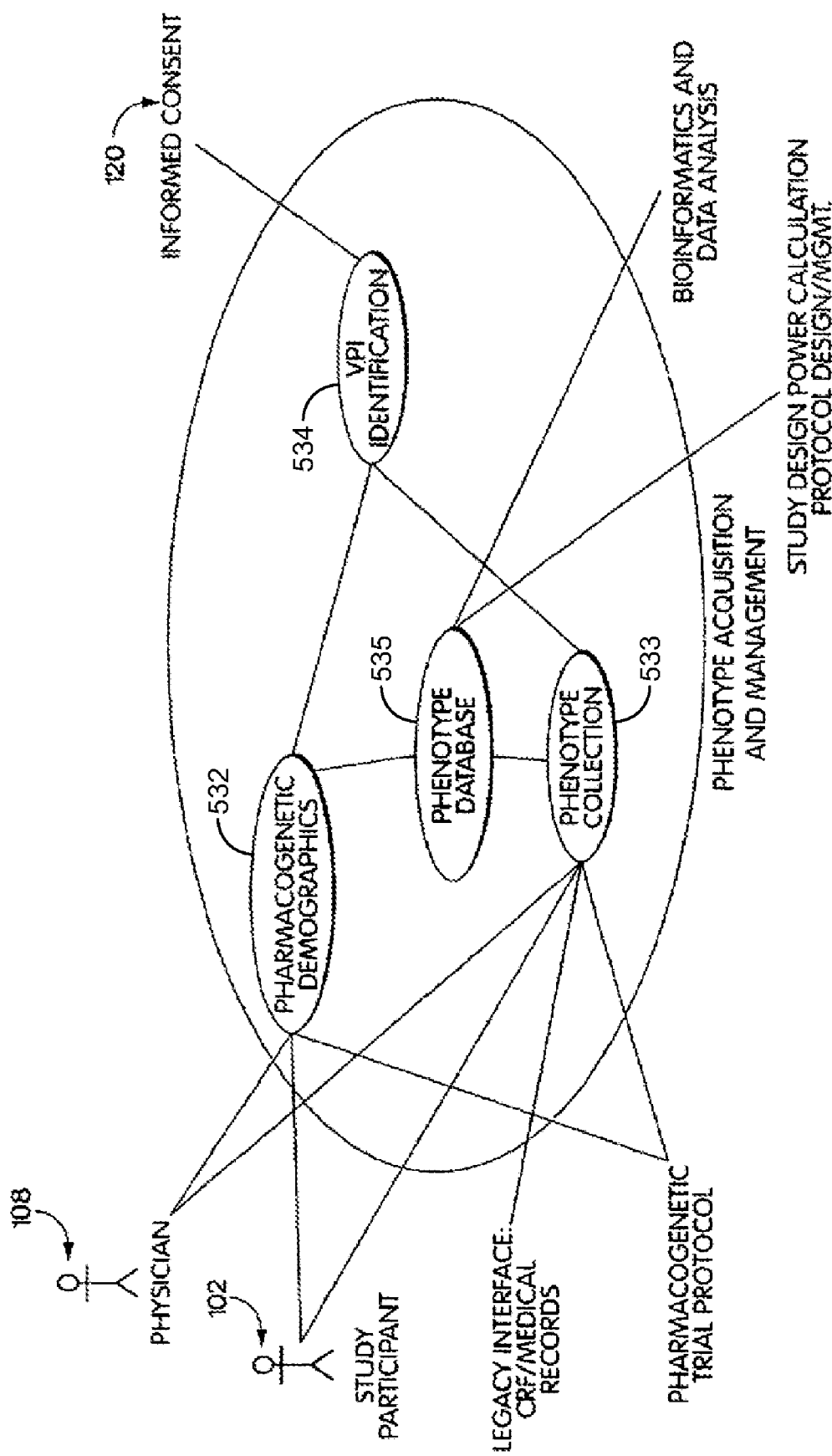
FIG. 7 depicts a process for managing the entry of phenotypic data for study participants.

FIGS. 6 and 7 depict further processes that may benefit from the systems and methods described herein. In particular, FIGS. 6 and 7 depict respectively a process 110 for genotyping management and a process 120 for phenotype acquisition and management.

FIG. 6 illustrates an exemplary embodiment of a genotyping management protocol for a genotyping tracking system 542 of the subject DICP system 10. Genotyping 526 of samples will often take place in genotyping labs. Upon the initiation of a genotyping request, the appropriate samples are retrieved 527 from their corresponding sample storage facility and shipped to the genotyping lab. Upon receipt, the genotyping lab is to proceed by following the "genotyping protocol" 525 which is part of the study protocol and defines the sequence of actions to be performed. The genotyping lab gets access to the appropriate genotyping protocol through the barcodes 529 (or numeric ids) on the received samples. The results of genotyping process are reported back 530 to the DICP system 10, after going through a "format conversion" 528 component, if necessary, that translates them to the appropriate DICP-compliant data format. Similar to the Sampling Lab case described above, the DICP system 10 can compile and maintain a database 531 of genotyping labs.

In certain embodiments, the subject DICP system 10 will include a Phenotype Acquisition & Management protocol. As illustrated in FIG. 7, such a sub-system allows the entry of phenotypic data for the Study Participants 102. The type of data to follow and report, are defined in the study protocol and may include pharmacogenetic demographics 532 and VPI identification 534. The data may be stored in a phenotype database 535. The collection 533 of all that data can be considered the "study-specific medical record" (SSMR) of the Study Participant. The DICP system 10 can provide a "Universal Medical Record Model" (UMRM), e.g., in accordance with existing standards, which can describe various phenotypic traits. For each trait, the UMRM can contain information like (i) the trait name (e.g. "Blood Pressure"), (ii) the associated value type (e.g., "numeric"), (iii) permissible ranges (E.g., "Positive, less than 40"), etc. The SSMR can be defined (on a study basis) as the appropriate subset of the UMRM.

Updating the SSMR of a Study Participant, is typically only allowed to be done by authorized Persons (e.g. a physician) that have appropriate Proxy rights on the Study Participant's account.

Figure 8:
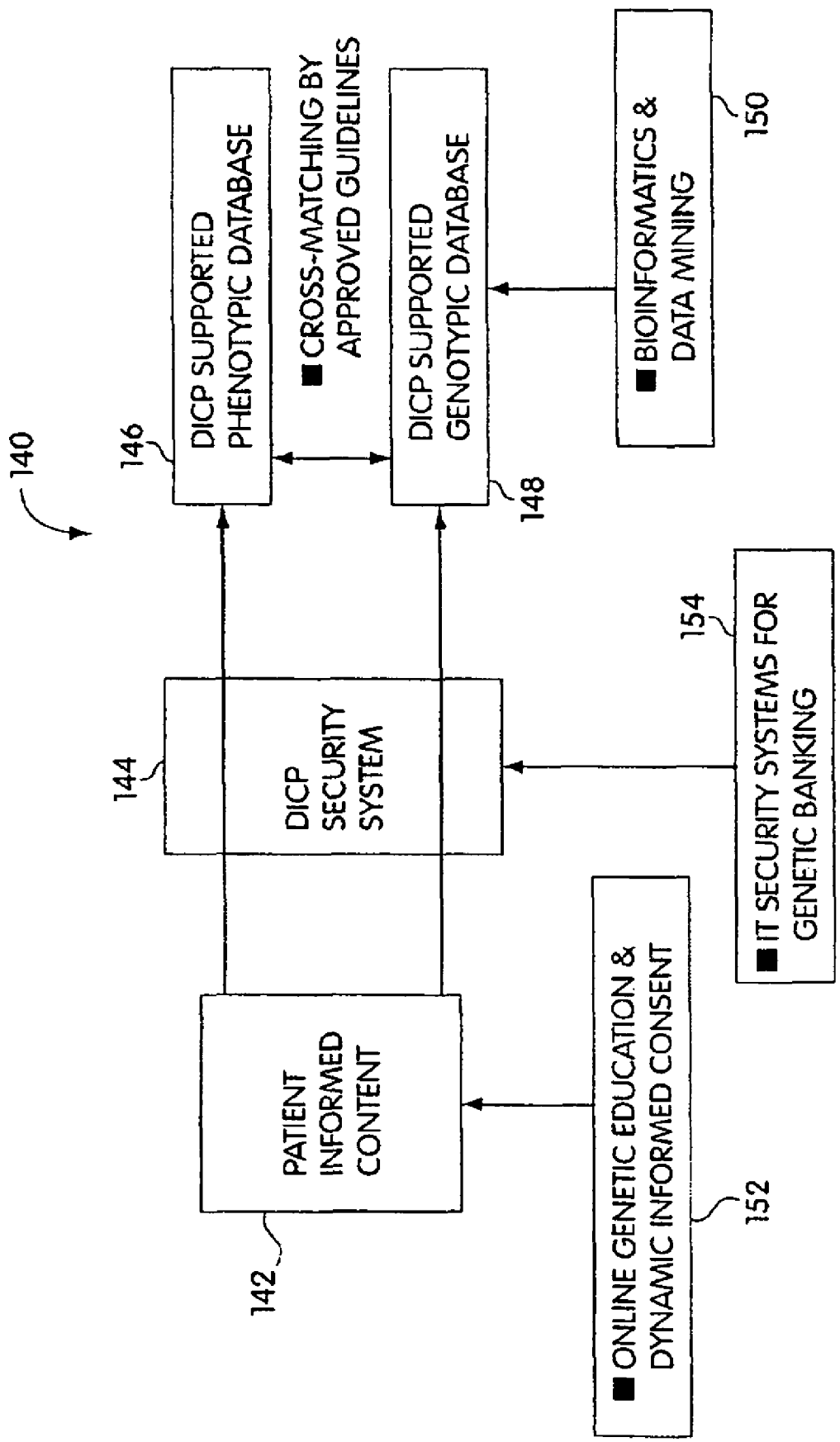
FIG. 8 illustrates an exemplary embodiment of the subject system for use in managing the informed consent processes of a genetic trial.

FIG. 8 illustrates an exemplary embodiment of the subject system for use in managing the informed consent processes of a genetic trial and where there is a DICP supported phenotypic database 146 and a DICP supported genotypic database 148. These databases 146 and 148 may be generated according to the processes described with reference to FIGS. 6 and 7. It will be apparent to those of skill in the art that a DICP supported sample database may also be provided, as well as databases containing other types of data. Thus, in the embodiment of FIG. 8 it can be seen that different components of a computer supported study or action may include or use the DICP systems described herein. In this embodiment, the informed consent 142 is linked, via the trusted intermediary, with genotypic and/or phenotypic data derived for the patient. In the process of obtaining the consent of the patient to the use of such data, certain embodiments of the subject system 140 can be set up to obtain varying levels of consent from the patient, e.g., which may effect to whom access is given and how a certain portion of the patient's data may be used. For instance, the DCIP system 140 can provide a controlled interface to the databases for bioinformatics analysis. The bioinformatics tools 150 can be provided as part of the DCIP system 140, or can be that of a third party on whose behalf consent for such analysis has been obtained from the patient. Such components/interfaces of the system 140 can provide advanced tools and algorithms for analyzing and correlating genotypic and phenotypic data.

The invention now being generally described, it will be more readily understood by reference to the following examples which are included merely for purposes of illustration of certain aspects and embodiments of the present invention, and are not intended to limit the invention.

Example 1

Receiving and Signing of Informed Consent Form

A. Use Case Diagram

This use case allows the study participant to access the Informed Consent Form (ICF) and Questionnaire online or by postal mail.

Study participant receives the ICF and Questionnaire by mail if desired. He must sign and mail the ICF and questionnaire back to DICP. This can be done online by pressing "I Accept" button and filling the questionnaire online. A notification for signing an ICF for a particular study is posted in the message box of the Study participant's page on the portal.

For the ICF to be valid, it has to returned and signed before its expiration date.

While requesting ICF by postal mail, study participant can specify if he wants to receive educational material along with ICF.

Questionnaire is optional and part of the ICF. Filling the questionnaire is not mandatory.

B. Basic Flow

| Participant Action | System Response |
|---|---|
| 1. Potential Participant logs into the Study Participant portal. | 2. System displays a pending request for signing the Informed Consent Form along with the ICF expiration date for the study he's participating in. |
| 3. Participant clicks on the notification message for signing ICF. | 4. System displays a screen with three options:<br>a. Generate a printable ICF<br>b. Receive ICF by Mail<br>c. Sign On-line<br>When actor selects any of the above options a barcode specific to the actor and study for which he is signing ICF is generated by the system.<br>This barcode along with it's corresponding human readable number will appear on the top of all the pages of ICF and questionnaire. |

C. Generating a Printable ICF

| Participant Action | System Response |
|---|---|
| Participant selects "Generate Printable ICF" | System generates a read-only PDF file of the ICF and questionnaire which can be downloaded and printed.<br>System also displays message explaining downloading and configuration instructions for Acrobat Reader for reading and printing PDF files.<br>System is notified that an ICF has been printed and ICF responding workflow is invoked. Scavenger will check on all ICF's that have not been received yet.<br>The generated PDF file also has the return address of DICP where the form needs to be submitted. |
| Participant displays the PDF file generated in the Step 2. Participant can print the file or save it on his local system for later printing. After signing the ICF he mails it to the DICP. | |

D. Receiving ICF/Educational Material by Mail

| Participant Action | System Response |
|---|---|
| Participant selects "Receive ICF by Mail" option in the step 4. | System retrieves the mailing address from the actor's record and displays for confirmation. Participant has an option to edit the mailing address. This address is not updated in his system record. System checks if this is first time, |

-continued

| Participant Action | System Response |
|---|---|
| | Participant is given an option of receiving the educational material along with ICF. |
| Participant has a choice of saying, "Yes" to receiving offline educational material. Presses the "Submit" button. | System checks for the validity of the address specified by the Participant. If incorrect, a corresponding error message is displayed with an option to update. Otherwise a request to third party vendor for mailing the ICF form/Educational material (if relevant) is triggered. |
| Participant receives the ICF/Questionnaire and Educational material by mail. Participant fills in the questionnaire signs ICF and mails it back to DICP. | |

E. Signing ICF On-line

| Participant Action | System Response |
|---|---|
| Participant selects "Sign On-line" | System displays the questionnaire, which needs to be filled by the Participant. Questionnaire is optional component of ICF. |
| Participant optionally fills in the questionnaire and presses submit button. | System displays the ICF form with the "I Agree" and "I Don't Agree" buttons. |
| Participant presses the "I Agree" button. | System displays confirmation box and if actor accepts that an acknowledgement page is displayed. The corresponding "Acceptance" workflow is triggered. |
| Participant presses the "I Don't Agree" button. | System displays confirmation box and if actor confirms to disagree an appropriate message is displayed. The "Dissent" workflow is triggered. |

F. Alternate Flow: System has Returned an Invalid Address Message Against what the Actor Entered

| Participant Action | System Response |
|---|---|
| | System will generate a message to the actor that the address they have entered does not match with the address on file. |

G. Alternate Flow: Participant Requests Only ICF by Mail

| Participant Action | System Response |
|---|---|
| Participant edits the address and presses the "Submit" button. | System checks for the validity of the address specified by the actor. If incorrect, a corresponding error message is displayed with an option to update. Otherwise a request to third party vendor for mailing the ICF form |
| Participant receives the ICF/Questionnaire by mail. Participant fills in the questionnaire signs ICF and mails it back to DICP. | |

The processes described above pictorially can be engineered as computer process running on a computer server. For example, FIG. 9 depicts one process 200 that may be representative of a computer process running on a computer server and being capable of providing educational material to a study participant or prospective study participant. As shown in FIG. 9 the process 200 begins a step 202 wherein it proceeds to step 204 wherein the actor selects the study and then selects the educational material that they wish to view or have to view. In step 206 the system displays the materials to the actor and in step 208 the actor selects additional desired educational material. The request for material is reviewed in decision block 210 wherein if the information is online the process 200 in steps 212 and 214 displays the online information to the actor and the actor can review it and the process can end at step 216. Alternatively, if during decision block 210 it is determined that the material is not online, the process 210 can proceed to step 218 and 220. Wherein the offline material is available and can be sent through the process beginning at step 222 or the message in step 220 can be broadcast typically indicating that the information is no longer available.

However, if in step 218 the materials are determined to be offline and available the process 200 can proceed to decision block 222. In decision block 222 the process can determine whether or not the study participant has already reviewed all the material that they can receive offline, if yes, they can be told so in step 240. Alternatively, if no, the actor may be provided with three options. These three options are set out in decision blocks 225,226 and 227. Typically, to maintain anonymity for the prospective study participant the process can choose to mail the information to the physician's address. Alternatively, the subject can choose to have the information mailed to their own address in a file or can have the information sent to an alternative address. In either case the process in step 228 confirms that the mailing address is correct and once that information is concerned the process proceeds to steps 229, 230, 231 and 232 wherein the submission request is reviewed, confirmed, recorded and noted for the purposes of validating the conformed consent procedure. However, if the step 228 determines that the mailing address is incorrect then the process provides several steps 234, 235 and 236, wherein the prospective study participant can amend the mailing address.

Figure 10:
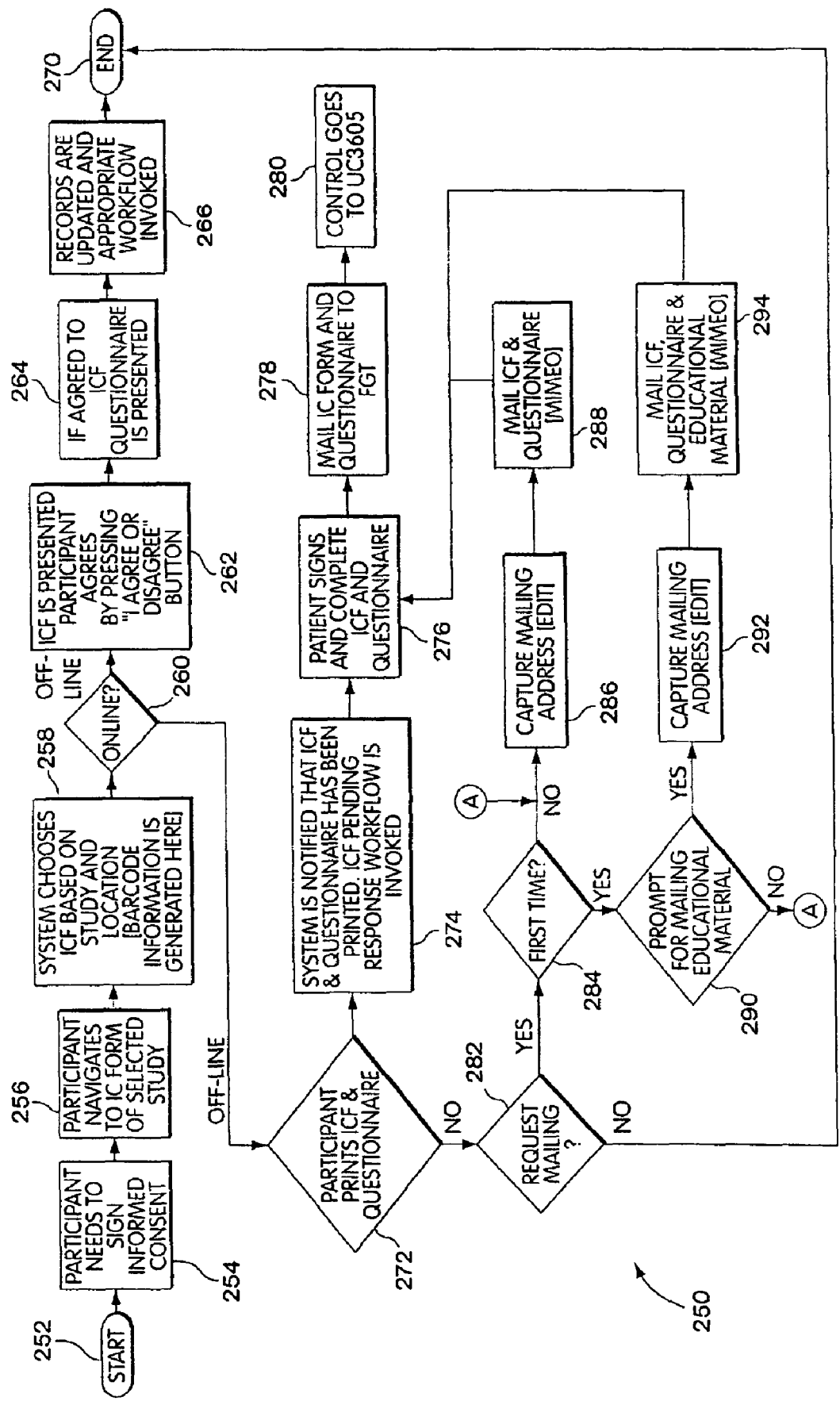
FIG. 10 depicts a process for providing a participant with an ICF for signature.

FIG. 10 depicts a computer process 250 for having an informed consent form be executed, or signed, by the human subject and returned to the system. Specifically the process 250 begins with the steps 252, 254, 256 and 258 wherein the process determines that the participant needs to sign a informed consent form, allows the participant to navigate to the informed consent form for the selected study and allows the system to choose the informed consent form based on the study and location that is relevant to the participant. If the form is online then in step 260 the process transfers the steps 262,264 and 266 wherein the online form is presented to the participant. In the depicted process the form is provided with a "click wrap" agreement that allows the user to execute the agreement by clicking a button "I agree". In alternative practices different kinds of execution may be employed such as digital signatures, biometric identity verifications and authorizations and other similar types of processes.

Once the form is executed the process 250 can record the updated grant of consent and the process may end at step 270. At the decision block 260 however, it may be determined that the informed consent form necessary is not online, in this case the process can proceed to step 272 wherein the participant prints out the ICF and the questionnaire and the system understand that the form has been printed out and the patient in step 276 signs and completes the ICF and the questionnaire and mails the ICF and questionnaire back to the biomedical professional, a trusted third party, or some other identity. In step 280 an offline process may be employed for entering the form into the database 14 of the system. As further shown in FIG. 10, the process may include a step 282 wherein there is a requested mailing. If this is the first time that something has been mailed then it may be determined that the documents may be mailed to the human subject. Alternatively, in steps 290,292 and 294 the participant may be prompt to receive a mailing of educational materials. If they accept the educational materials then again the process will capture the mailing address and mail off the educational materials along with the informed consent form and the questionnaire to the participant. In alternative embodiments where educational material have to be either sent and/or reviewed by the participant, there may be no option step for the user to only receive the informed consent form and the questionnaire and instead will have to receive the educational materials as well.

Figure 11B:
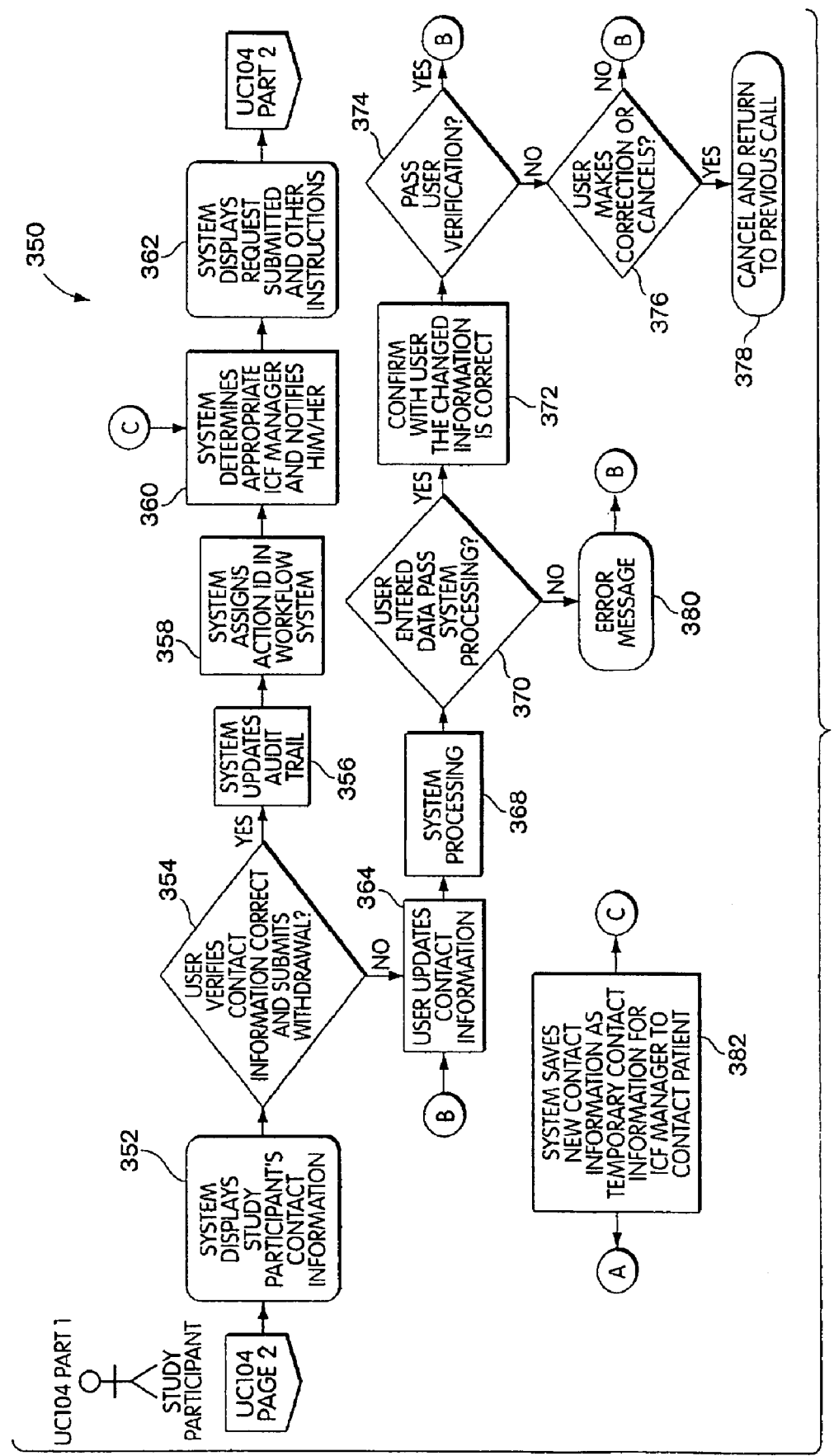
Figure 11C:
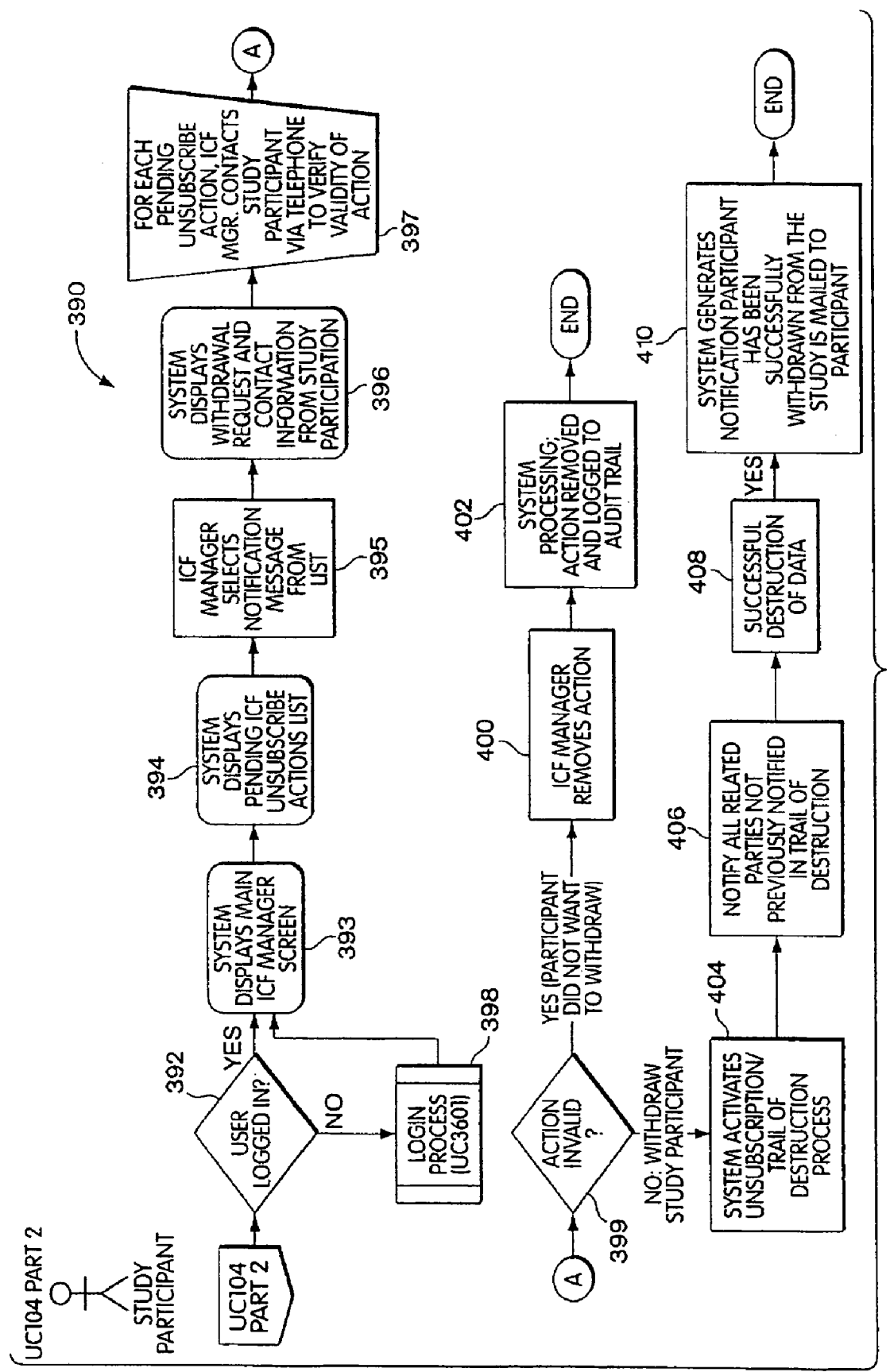

FIGS. 11A, 11B and 11C depict processes for allowing a study participant to withdraw from a study, an action, or a procedure. It will be understood that the processes depicted in FIGS. 11A through 11C are representative of processes that the invention provides to allow a user to change the grant of consent they have provided. In the processes described hereinafter, the study participant chooses to withdraw or eliminate their grant of consent. However, in other processes the study participant may choose to expand, reduce, or otherwise change the grant of the consent that they had provided. Accordingly, it will be understood that the processes described below are merely representative of the types of processes that may be provided by the invention and variation to these example processes will be apparent to those with ordinary skill in the art.

Turning to FIG. 11A, a process 300 is depicted that begins in a step 302 and proceeds to step 304. At step 304 the process 300 determines whether the user is logged in. If the user is logged in, the process proceeds to step 306. At step 306, the system displays a main study participant portal screen. The portal screen may be understood to be a webpage provided by the system to the user for the purpose of presenting the study participant with information that is relevant to the managing of the participants talent. The portal may be a web portal of the kind provided to allow for authorized access to different services and information supported by the portal. To this end, in one embodiment, the portal may be realized as a secure web server capable of transferring HTTP compliant data across a data network. The design and development of such portals is known to those with skill in the art and any suitable portal may be practiced with the present invention without departing from the scope thereof.

As further shown in FIG. 11A, the study participant may employ the portal in step 308 to navigate to the personal account information maintained by that participant. The portal employed in 308 may be similar to the portal provided by portal process 20 depicted in FIG. 1. In step 310, the system displays the specific studies that the participant has registered in. In the particular practice depicted by FIG. 11A, the user is provided a virtual private identity code that may be employed by the system has an index key into a database that stores information associated with that key and therefore that user. The virtual private identity key may be kept secret by the user, thereby providing a level of security to the database that stores information about that user. In step 312, the user may select a pharmacogenetic study of interest. The system then may display the selected pharmacogenetic study information and link to the appropriate informed consent form. In step 318, the user chooses to withdraw from a study. After that, the process can proceed to step 320 wherein the system displays action consequences and confirms the actions of the study participants. If in step 322 the user verifies their request to withdraw, then the process may proceed to process 350 depicted in FIG. 11B. Alternatively, if the user chooses not to withdraw, then the process may proceed from step 322 to step 314.

However, upon an indication of a request to withdraw, the process 350 depicted in FIG. 11B may be invoked. In process 350 the study participant is displayed, in step 352, contact information. At decision block 354, the user can verify that contact information and correct it if necessary. In step 356, the system can update an audit trail. The audit trail will be representative of the actions taken by the study participant through the portal site. In step 358, the system can assign an action id in a workflow system and in step 360, the system can determine the appropriate manager of the study and notify him of the withdrawal. In step 362, the system can display a request that has been submitted (and other instructions as well). After step 362, the process may proceed to process 390 depicted in FIG. 11C. Returning to decision block 354, if the user wishes to update their contact information, the process at 354 may proceed to step 364. The process in subsequent steps 368,370 and 372 may choose to update and confirm their change of system address information. In decision blocks 374 and 376, the process can require a verification step to allow the address change to occur. If verified, the address can be changed. If not, the system can cancel the process. The saving of the information is depicted in step 382 shown in FIG. 11B.

Turning to FIG. 11C, the process 390 is depicted as showing step 392 where it is determined whether the user is logged in. Between 392 and 398, the determination is made and the process 390 proceeds to 393. At 393, the system displays the main informed consent form manager screen. The process 390 may then proceed to step 394 wherein the system displays a pending informed consent form. In step 395, the informed consent form manager can select notification messages from a list and in step 396 the system can display the withdrawal request and contact information provided from study participant. At step 397, for each pending unsubscribed action, the informed consent form manager contacts the study participant vis a vis a telephone to verify the validity of the action. If the action is invalid, the process at step 399 proceeds to steps 400 and 402 wherein the ICF manager removes the unsubscribed action and amends the audit trail. Alternatively, if the action is not invalid, and therefore valid, the process proceeds to steps 404, 406, 408 and 410 wherein the system activates an unsubscribed process, that notifies all related parties of the action, and there is a successful destruction of data step 408. In step 410, the system generates notification to the participant indicating that they have been withdrawn and that their data has been destroyed.

FIG. 12 depicts a process that the systems and methods described herein may employ for receiving a hard copy of the signed informed consent form from a prospective study participant. In particular, FIG. 12 depicts a process 420 that begins at step 422. The process proceeds to step 424 wherein the person, in this case the prospective study participant or study participant that is interested in changing, including expanding or reducing the grant of consent that they earlier provided, receives a document from either the group running the study or from a trusted intermediary. In step 426 the person can execute the document typically by signing it and dating it and sends it back to the appropriate authority. In the process 420 the appropriate authority may be the trusted intermediary party or may be some other party such as the clinical site where the study participant will give samples or other information.

In step 428 the authorized entity receives the form and in step 430 logs the form into the system 10. And in step 432 indicates that the form has been entered into the system. The process 420 then proceeds to step 434 wherein a representative reviews the documents for signature. At decision block 436 the process determines whether the persons signature is accepted. If it is accepted the process then checks in step 438 whether the witness signature is accepted. The option of using a witness may be available in some practices of the invention however it is not always required. If the signatures are accepted the process proceeds to step 440 wherein an authority scans the document image into the document database based on a barcode provided with the informed consent form. At step 442 the process determines whether consent has been granted. This step can involve verifying other kinds of criteria to consent such as has the form been completed and returned within the appropriate time frame, has the form been sent in duplicate, and other kinds of criteria. If the answer is yes then the process 420 can proceed to step 444 wherein a representative at the entity activates the document consent record and reports questionnaire results if this are required. The process then proceeds to step 446 wherein the system updates the audit trail and workflow. If at the decision block 436 it is determined that the persons signature is not accepted then the process may proceed to steps 448 and 450 wherein a representative reviews the remainder of the document for other errors and the representative send the person a new document requesting their signature. Optionally, the new form may be accompanied by a cover letter than outlines the errors that arose in the original document.

Figure 13:
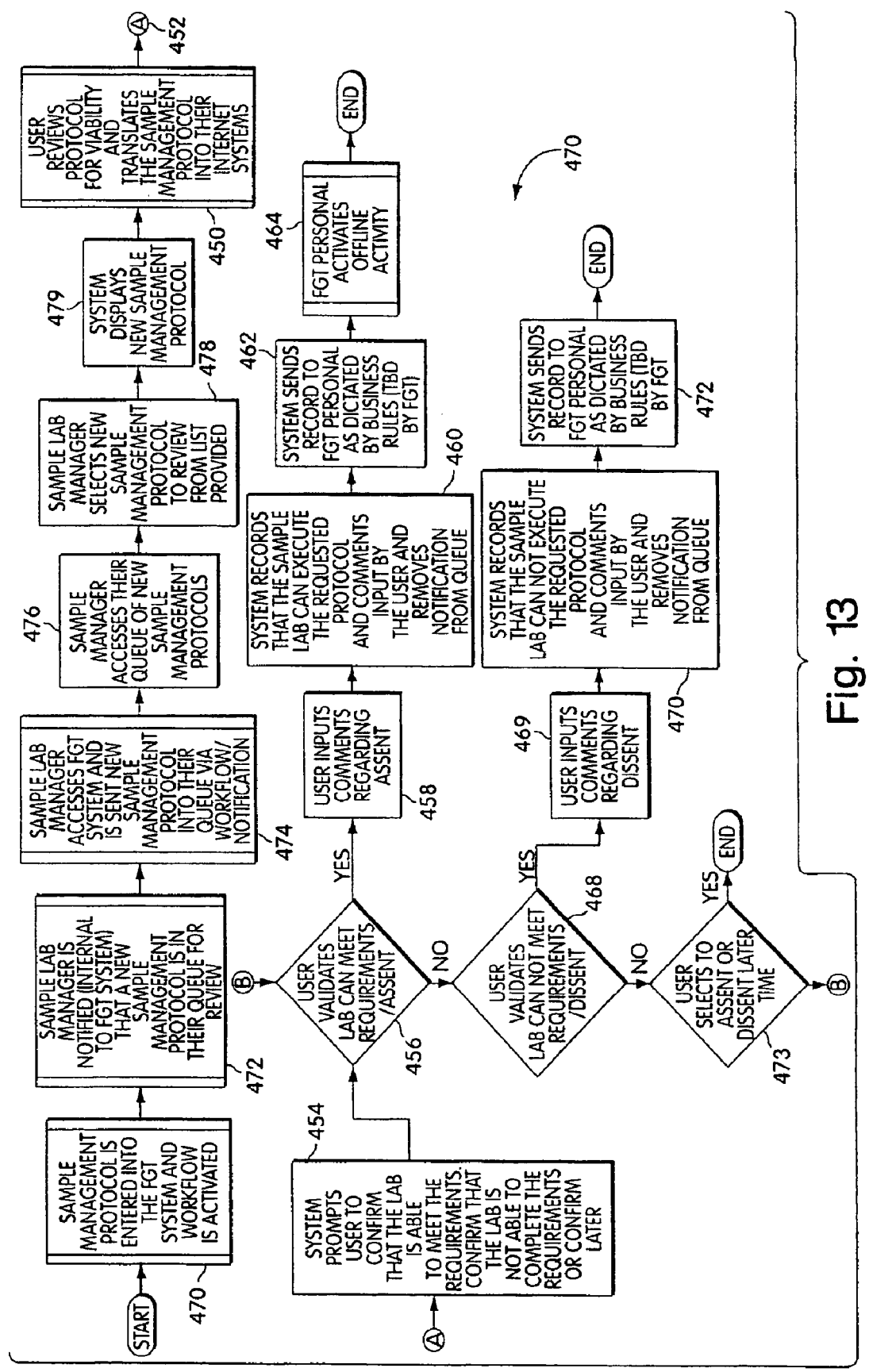
FIG. 13 depicts a process for controlling access to new sample management protocols.

Turning now to FIG. 13 a further process that may be employed by the system depicted in FIG. 1 is depicted. Specifically, FIG. 13 depicts a process 470 that controls the access of new samples being managed according to the selected protocol. The process 470 includes a step of entering the sample management protocol into the system 10 and activating workflow. At step 474 the sample lab manager may be notified that a new sample management protocol has been put in their queue for review. The sample lab manager, at step 476 may access the system 10 and be sent the new sample management protocol into their queue via workflow notification. The sample manager accesses their queue of sample management protocols and in 479 the sample lab manager selects the new sample management protocol to review from the list provided. At step 450 the system displays a sample management protocols and in step 452 the user reviews protocol for visibility and translates the sample management protocol into their internal system.

After step 452 the process may proceed to process 454 wherein the system prompts the user to confirm that the lab is able to meet the requirements and confirm that the lab is not able to complete the requirement or to identify the fact that they will confirm this information later. At decision block 456 the user validates that the lab can meet the requirements. In step 458 the user inputs comments regarding their ascent and in steps 460-464 the system records that the sample lab can execute the requested protocol sends a notice to the system, if such notice is dictated by business rules and personnel then attend to offline activity. Alternatively, if act decision block 456 the process determines that the lab can not meet the certain requirements set out the process proceeds to step 468 wherein the user validates that the lab can not meet the requirement. If such validation occurs then the process in steps 469-472 inputs comments regarding the descent records that the sample can not execute the requested protocol and the system sends a record to the appropriate personnel if such a notice or record is dictated by business rules. Alternatively, if at step 468 the user can not confirm that the requirements can not be met the system proceeds to step 473 wherein they indicate that at a later time the user will select to ascent or decline.

As discussed above, the dynamic informed consent process and systems described herein may be realized as a software component or components operating on a conventional data processing system such as a Unix workstation. In that embodiment, the DCIP system may be implemented as a C language computer program, or a computer program written in any high level language including C++, Fortran, Java or basic. Additionally, in an embodiment where microcontrollers or DSPs are employed, the DCIP systems may be realized as a computer program written in microcode or written in a high level language and compiled down to microcode that can be executed on the platform employed. The development of such systems follows from techniques known to those of skill in the art, and such techniques are set forth in Digital Signal Processing Applications with the TMS320 Family, Volumes I, II, and III, Texas Instruments (1990). Additionally, general techniques for high level programming are known, and set forth in, for example, Stephen G. Kochan, Programming in C, Hayden Publishing (1983). It is noted that DSPs are particularly suited for implementing mathematical functions, including encryption functions. Developing code for DSP and microcontroller systems follows from principles well known in the art.

Additionally, although FIG. 1 graphically depicts the DCIP systems 10 as an arrangement of interconnected functional block elements, it will be apparent to one of ordinary skill in the art that these elements can be realized as computer programs or portions of computer programs that are capable of running on a data processor platform to thereby configure the data processor as a system according to the invention. Moreover, although FIG. 1 depicts the system 10 as an integrated unit, it will be apparent to those of ordinary skill in the art that this is only one embodiment, and that the invention can be embodied as a group of computer programs that operate on different separate machines, including machines located at different physical locations, such as machines located at a clinical site and machines located at the site of a trusted intermediary, with the different sites communicating for example across a data network such as the Internet.

Accordingly, the systems and methods described above are merely representative of the different embodiments that may be realized from the invention, and other systems and applications may be realized, including for example systems for allowing attorneys to identify member of a particular class that may have a common cause of action, systems for organizing clinical trials, post-marketing surveillance, and patient recruitment for genetic and genomic research, as well as the delivery of molecular diagnostics and therapeutics.

The invention claimed is:

1. A computer-implemented process for obtaining an informed consent from a human subject for an action, the process comprising:

receiving, utilizing a first computer process, data representative of at least one of demographic, medical, genetic, and biological information of the human subject;

storing the received data representative of at least one of demographic, medical, genetic, and biological information of the human subject into a data memory;

upon contacting the human subject, receiving a first grant of consent, wherein the first grant of consent is a grant of informed consent to be associated with the stored data representative of at least one of demographic, medical, genetic, and biological information of the human subject, utilizing a second computer process, wherein the grant of informed consent indicates at least one select type of activities and uses to which the human subject agrees or consents;

receiving a second grant of consent, wherein the second grant of consent is consent to re-contact the human subject to be associated with the stored data representative of at least one of demographic, medical, genetic, and biological information of the human subject;

receiving a request to perform an action on the data representative of at least one of demographic, medical, genetic, and biological information of the human subject;

in response to the request, determining the first grant of informed consent is insufficient for the action, utilizing a third computer process; and upon determining that the first grant of informed consent is insufficient for the action, re-contacting the human subject to request the human subject to change the first grant of informed consent, wherein the first, second and third computer processes are performed on one or more computing devices.

2. The computer-implemented process of claim 1, wherein the data representative of at least one of demographic, medical, genetic, and biological information consists of medical and genetic information.

3. The computer-implemented process of claim 1, wherein a trusted third party controls access to the stored data representative of at least one of demographic, medical, genetic, and biological information of the human subject.

4. The computer-implemented process of claim 3, wherein re-contacting the human subject to request the human subject to change the first grant of informed consent comprises having the trusted third party re-contact the human subject.

5. The computer-implemented process of claim 4, further comprising:

encrypting the stored data representative of at least one of demographic, medical, genetic, and biological information of the human subject in the data memory.

6. The computer-implemented process of claim 5, wherein receiving a request to determine whether the grant of informed consent is sufficient for the action includes querying the encrypted stored data representative of at least one of demographic, medical, genetic, and biological information of the human subject.

7. The computer-implemented process of claim 1, wherein storing the received data representative of at least one of demographic, medical, genetic, and biological information of the human subject into a data memory includes receiving portions of the data representative of at least one of demographic, medical, genetic, and biological information of the human subject as clear text and portions in an encrypted format, such that the human subject may control which portions of the stored data representative of at least one of demographic, medical, genetic, and biological information of the human subject may be searched by an interested party.

8. The computer-implemented process of claim 1, further comprising:

receiving re-contact data for re-contacting the human subject; and storing the received re-contact data for re-contacting the human subject in association with the stored data representative of at least one of demographic, medical, genetic, and biological information of the human subject.

9. The computer-implemented process of claim 8, wherein the stored re-contact data for re-contacting the human subject is selected from the group consisting of an e-mail address, a post address, a patient code assigned to the human subject, an address for the human subject's physician, and identity information for the human subject.

10. The computer-implemented process of claim 1, wherein re-contacting the human subject to request the human subject to change the first grant of informed consent includes contacting the human subject by a method selected from the group consisting of e-mail, mail, putting a notice on a bulletin board, contacting the human subject's physician, telephone, and using a portal the human subject is authorized to access.

11. The computer-implemented process of claim 1, wherein re-contacting the human subject to request the human subject to change the first grant of informed consent includes delivering a form for changing the grant of informed consent.

12. The computer-implemented process of claim 1, further comprising:
    generating a request to change the first grant of informed consent associated with the stored data representative of at least one of demographic, medical, genetic, and biological information of the human subject.

13. The computer-implemented process of claim 12, wherein receiving a request to change the first grant of informed consent associated with the stored data representative of at least one of demographic, medical, genetic, and biological information of the human subject includes expanding a granted level of access, reducing the granted level of access, or eliminating access.

14. The computer-implemented process of claim 1, further comprising:
    presenting a notice identifying new actions that the human subject may want to be part of.

15. A computer system for controlling consents of a human subject, the system comprising:
    a database providing secure storage of one or more of demographic, medical, genetic, and biological information of the human subject, wherein the database includes a storage location for storing information representative of a first grant of consent and a second grant of consent, wherein the first grant of consent is a grant of informed consent and wherein the second grant of consent is a grant of consent to re-contact the human subject;
    a first querying component configured to query the one or more of demographic, medical, genetic, and biological information of the human subject based upon provided parameters, and query information representative of the first grant of informed consent and the second grant of consent to re-contact the human subject;
    a receiving component configured to receive a request involving the one or more of demographic, medical, genetic, and biological information of the human subject;
    a first determining component configured to determine a third grant of consent is required to satisfy the request, wherein the third grant of consent is a grant of informed consent;
    a second determining component, utilizing a computing device, configured to determine that the human subject provided the second grant of consent to re-contact the human subject;
    a re-contacting component configured to contact the human subject;
    a portal component configured to present the human subject with information regarding changing the first grant of informed consent; and
    a consent component configured to receive the third grant of consent from the human subject.

16. The computer system of claim 15, wherein the system is maintained and operated by a trusted third party.

17. The computer system of claim 16, wherein the first grant of informed consent includes restrictions relating to whether an interested party may query the one or more of demographic, medical, genetic, or biological information of the human subject.

18. The computer system of claim 17, wherein a second querying component is configured to conduct an initial process that identifies which of the one or more of demographic, medical, genetic, or biological information of the of human subject may be queried.

19. The computer system of claim 15, wherein the storage location for storing information includes information representative of previously collected biological samples, medical data, or genetic data.

20. The computer system of claim 15, further comprising:
    an encryption component, wherein the encryption component encrypts the demographic, medical, genetic, or biological information of the human subject.

21. The computer system of claim 20, wherein the first query component includes means for performing a query on the encrypted demographic, medical, genetic, or biological information.

22. The computer system of claim 15, further comprising:
    an enrollment component, wherein the enrollment component is configured to receive communications from the human subject and to determine whether to enroll the human subject in an action or study.

23. A computer-implemented method for permitting a study participant to change a grant of informed consent, the method comprising:
    determining a study participant is logged in;
    upon determining that the study participant is logged in, presenting a main study participant portal screen;
    receiving a request to navigate to personal account information of the study participant at a computing device via a secure network connection;
    presenting all virtual private identity-specific studies that the study participant is participating in or has participated in via the secure network connection, wherein the computing device determines the virtual private identity-specific studies for presentation;
    receiving a request to select a pharmacogenetic study of interest;
    presenting the selected pharmacogenetic study information including a first grant of informed consent of the study participant for the selected pharmacogenetic study; and
    receiving a request to alter the first grant of informed consent of the study participant for the selected pharmacogenetic study to a second grant of informed consent of the study participant for the selected pharmacogenetic study.

* * * * *